United States Patent
Tang et al.

(10) Patent No.: US 9,949,464 B2
(45) Date of Patent: Apr. 24, 2018

(54) TARGET MOLECULES FOR TRANSCRIPTIONAL CONTROL SYSTEMS

(71) Applicant: President and Fellows of Harvard College, Cambridge, MA (US)

(72) Inventors: Chung Yiu Jonathan Tang, Boston, MA (US); Constance L. Cepko, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 388 days.

(21) Appl. No.: 14/500,132

(22) Filed: Sep. 29, 2014

(65) Prior Publication Data

US 2015/0096066 A1   Apr. 2, 2015

Related U.S. Application Data

(60) Provisional application No. 61/884,346, filed on Sep. 30, 2013.

(51) Int. Cl.
*A01K 67/00* (2006.01)
*A01K 67/027* (2006.01)
*C07K 14/47* (2006.01)
*C12N 15/85* (2006.01)

(52) U.S. Cl.
CPC ...... *A01K 67/0275* (2013.01); *C07K 14/4705* (2013.01); *C12N 15/85* (2013.01); *A01K 2217/203* (2013.01); *A01K 2217/206* (2013.01); *A01K 2267/0393* (2013.01); *C07K 2319/71* (2013.01); *C07K 2319/80* (2013.01); *C12N 2830/002* (2013.01)

(58) Field of Classification Search
CPC .................. A01K 67/0275; A01K 2217/203
See application file for complete search history.

(56) References Cited

PUBLICATIONS

Naito et al. J Reprod Fert 113:137-143, 1998.*
Raina et al. Gene 96-100, 2015.*
Maeder and Gerbach. Official Journal for the American Society of Gene and Cell Therapy 24(3):430-446, 2016.*
Howden, CRISPR gene editing causes hundreds of unintended, off-target in Cosmos 2017. Printed from https://cosmosmagazine.com/biology/; pp. 1-7.*
Gaj et al. Trends in Biotechnology 31(7):397-405, 2013.*
Heintz, Nathaniel, "Gene Expression Nervous System Atlas (GENSAT)", Nature Neuroscience, 7(5), (2004), p. 483.

Ho, Steffan N., et al., "Dimeric ligands define a role for transcriptional activation domains in reinitiation", Nature, 382(6594), (1996), 822-826.
Kim, Douglas S., et al., "A Core Paired-Type and POU Homeodomain-Containing Transcription Factor Program Drives Retinal Bipolar Cell Gene Expression", The Journal of Neuroscience, 28(21), (2008), 7748-7764.
Kirchhofer, Axel, et al., "Modulation of protein properties in living cells using nanobodies", Nature Structural & Molecular Biology, 17(1), (Jan. 2010), 133-139.
Kirchhofer, Axel, et al., "Modulation of protein properties in living cells with nanobodies", Supplemental Information, Nature Structural & Molecular Biology, 17(1), (2010), 13 pgs.
Miyawaki, Atsushi, et al., "Fluorescent indicators for Ca2+ based on green fluorescent proteins and calmodulin", Nature, 388(6645), (1997), 882-887.
Olson, C. Anders, et al., "Design, expression, and stability of a diverse protein library based on the human fibronectin type III domain", Protein Science, 16(3), (2007), 476-484.
Pollock, Roy, et al., "Dimerizer-regulated gene expression", Current Opinion in Biotechnology, 13, (2002), 459-467.
Rivera, Victor M., et al., "Controlling Gene Expression Using Synthetic Ligands", Methods: A Companion to Methods in Enzymology, 14, (1998), 421-429.
Rothbauer, Ulrich, et al., "A Versatile Nanotrap for Biochemical and Functional Studies with Fluorescent Fusion Proteins", Molecular & Cellular Proteomics, 7(2), (2006), 282-289.
Rothbauer, Ulrich, et al., "Targeting and tracing antigens in live cells with fluorescent nanobodies", Nature Methods, 3(11), (2006), 887-889.
Sadowski, Ivan, et al., "GAL4-VP16 is an unusually potent transcriptional activator", Nature, 335(6190), (Oct. 6, 1988), 563-564.
Samson, Maria, et al., "Robust Marking of Photoreceptor Cells and Pinealocytes With Several Reporters Under Control of the Crx Gene", Developmental Dynamics, 238, (2009), 3218-3225.
Sato, Shigeru, et al., "Dkk3-Cre BAC Transgenic Mouse Line: A Tool for Highly Efficient Gene Deletion in Retinal Progenitor Cells", Genesis, 45, (2007), 502-507.
Sato, Shigeru, et al., "Dkk3-Cre BAC Transgenic Mouse Line: A Tool for Highly Efficient Gene Deletion in Retinal Progenitor Cells", Supplemental Information, Genesis, 45, (2007), 1 pg.
Tang, Jonathan C.Y., et al., "A Nanobody-Based System Using Fluorescent Proteins as Scaffolds for Cell-Specific Gene Manipulation", Cell 154, (2013), 928-939.
Zhou, X., et al., "Optimization of the Tet-On system for regulated gene expression through viral evolution", Gene Therapy, 13(19), (2006), 1382-1390.
Koide, A., et al., "Teaching an old scaffold new tricks: monobodies constructed using alternative surfaces of the FN3 scaffold", J Mol Biol. Jan. 13, 2012;415(2):393-405. doi:10.1016/j.jmb.2011.12.019, (2012), 20 pgs.
Kubala, M.H., et al., "Structural and thermodynamic analysis of the GFP:GFP-nanobody complex", Protein Sci. Dec. 2010;19(12):2389-401. doi: 10.1002/pro.519., (2010), 13 pgs.

* cited by examiner

*Primary Examiner* — Marcia S Noble
(74) *Attorney, Agent, or Firm* — Schwegman Lundberg & Woessner, P.A.

(57) ABSTRACT

The invention provides systems to control gene expression or activity using target molecules.

14 Claims, 14 Drawing Sheets
(14 of 14 Drawing Sheet(s) Filed in Color)

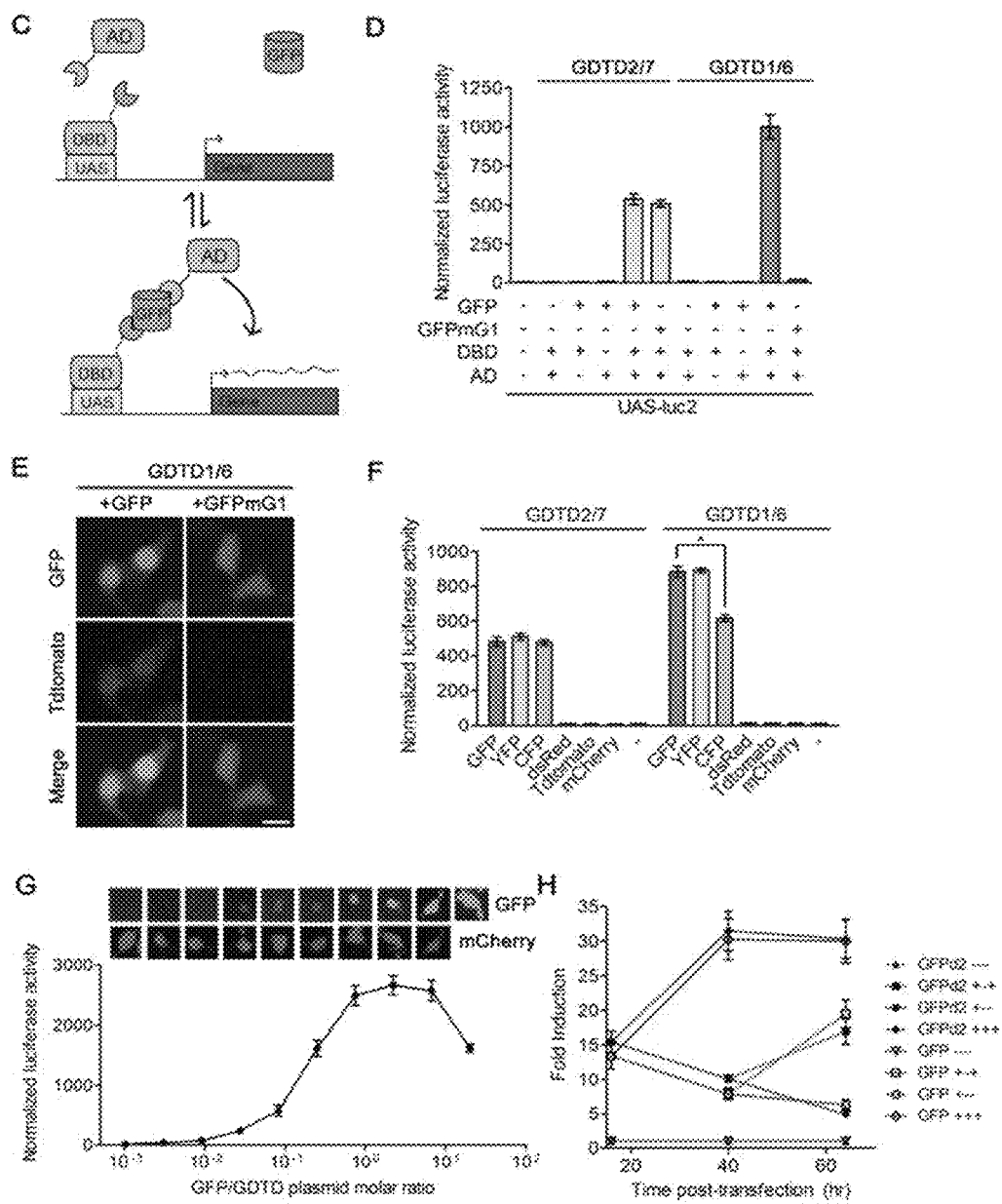
Figure 1 (contd.).

Figure 13.
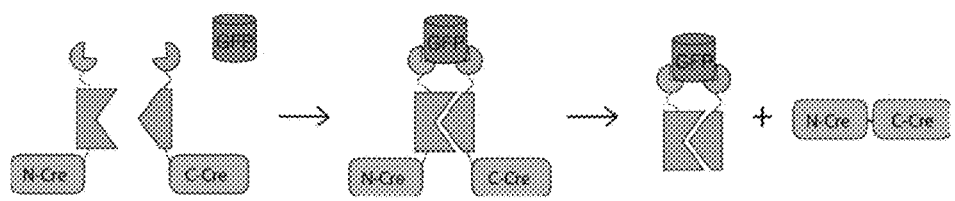
A GFP-dependent Cre-recombinase.
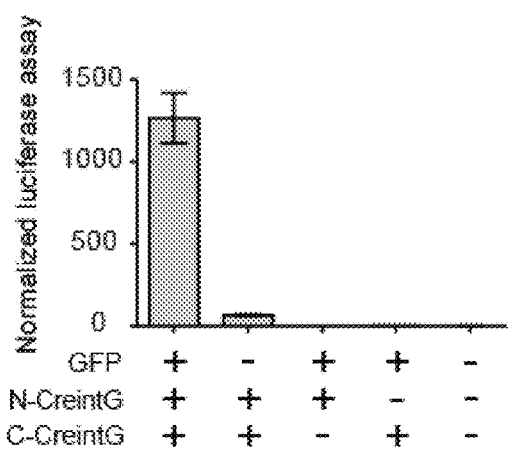
Figure 14. GFP-dependent activation of a floxed luciferase reporter in 293T cells. N-CreintG = N-Cre-intein-GBP fusion. C-CreintG = C-Cre-intein-GBP fusion.

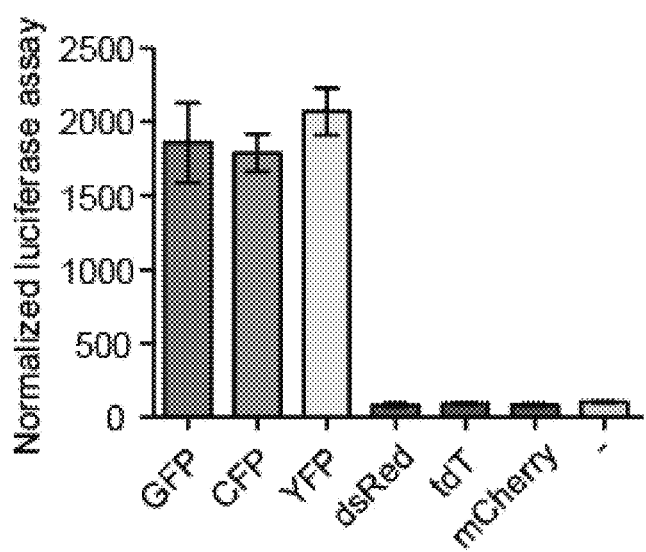
Figure 15. CRE-DOG can induce recombination of reporter in response to GFP, YFP and CFP, but not dsRed.

mCherry and tdTomato.

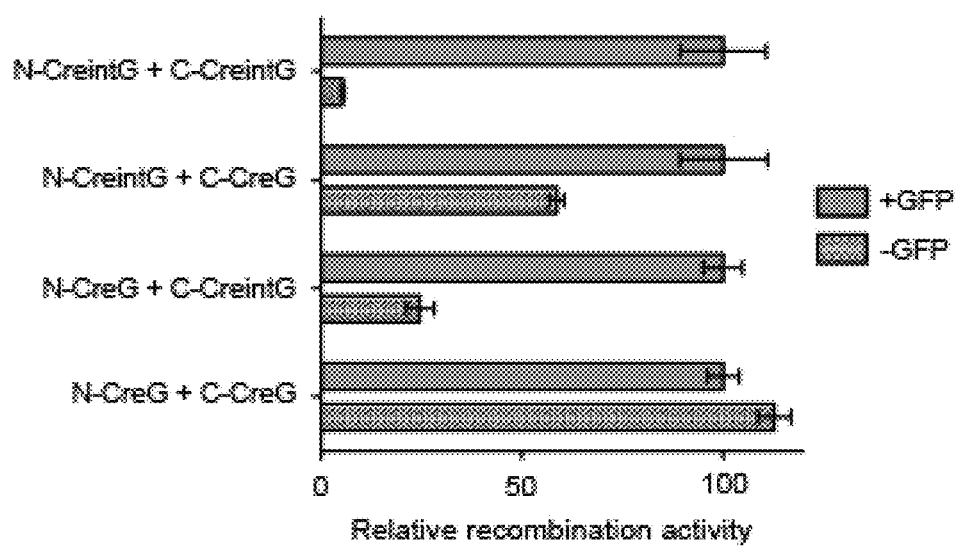

Figure 16. Intein domains play a role in the GFP-dependency of recombinase activity. Different fusion constructs bearing split-Cre fragments fused either directly to intein and GBP (N-CreintG and C-CreintG), or GBP only (N-CreG and C-CreG), indicate that both intein components play a role in conferring the fusion constructs with GFP-dependent recombination activity.

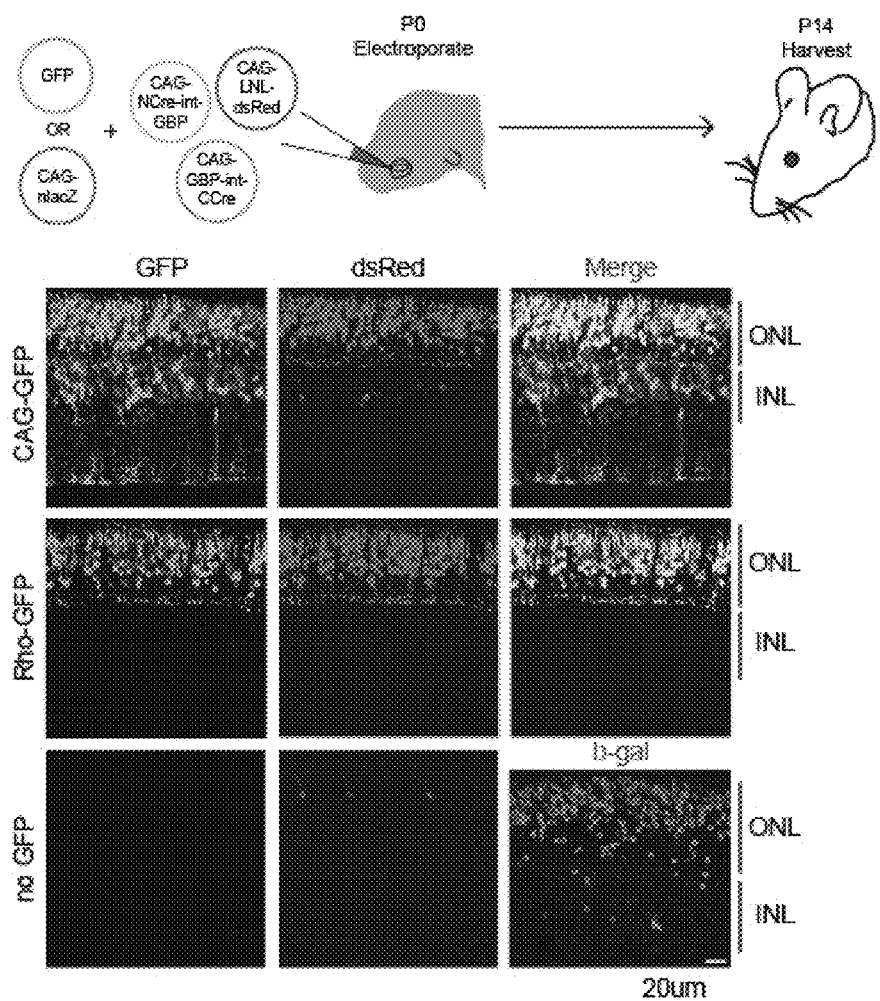
Figure 17 CRE-DOG induces GFP-dependent recombination in the mouse retina. A.) Schematic of experiment. B.) CAG-GFP C.) Rho-GFP D.) mGluR6-GFP. Electroporation of DNA plasmids encoding CRE-DOG components into the mouse retina, assayed 14 days post-natal birth.

TARGET MOLECULES FOR TRANSCRIPTIONAL CONTROL SYSTEMS

CROSS-REFERENCE TO RELATED APPLICATIONS

This application claims the benefit of the filing date of U.S. application Ser. No. 61/884,346, filed on Sep. 30, 2013, the disclosure of which is incorporated by reference herein.

BACKGROUND

The natural world is scoured for genomic products with desired properties for human applications. Artificially, novel RNA and protein functions can be achieved by the use of recombinant DNA technology to generate new biological entities. However, very little has been done to endow unmodified RNAs or proteins with novel biological functions. Artificially-derived antigen-binding proteins such as nanobodies have been used for the inhibition or degradation of intracellular target antigens. The inverse strategy of using artificially-derived antigen binding proteins linked to other molecules that promote enhanced activity of the resulting complex formed by the addition of an intracellular non-native antigen to activate synthetic devices, has apparently never been attempted. Fluorescent proteins are now used to label specific cell types and proteins in a wide range of organisms. The majority of GFP applications exploit GFP fluorescent properties to trace cellular processes such as gene expression and protein localization (Tsien, 1998; Chalfie et al., 1994; Ogawa et al., 1995; Miyawaki et al., 1997; Patterson et al., 2002; Berg et al, 2009). GFP is useful for these instances because it is extraordinarily inert in heterologous systems. It is freely diffusible in the cytoplasm, can enter the nucleus, has low cytotoxicity and few non-specific interactions with host proteins (Ogawa et al., 1995; Trinkle-Mulcahy et al., 2008).

SUMMARY

The invention provides a system that employs a target molecule, e.g., an exogenous molecule or an endogenous molecule, as a synthetic ligand that is useful to regulate expression or activity, including enzymatic activity (for instance, recombinase or protease activity) or cell-cell signaling, in vertebrate cells, such as mammalian cells or zebrafish cells. In one embodiment, the target molecule is one which has a low level of non-specific interaction with mammalian proteins. For example, optically detectable proteins, including GFP which is commonly used to visualize specific cell types in transgenic animals, or other proteins that are not native to a mammalian cell, or a cell type specific-molecule, may be employed as a synthetic ligand. As described herein below, in order to use untagged GFP for gene manipulation, GFP binding proteins (GBPs) derived from Camelid antibodies were employed to prepare GFP-dependent transcription systems. GBPs fused to other domains from other proteins, e.g., a DNA binding domain and a transcriptional activator domain, were introduced into existing transgenic GFP mouse lines and GBP activities were found to be tightly dependent on GFP expression. Since untagged GFP is freely diffusible and generally innocuous in heterologous systems, GFP, as well as other optically detectable proteins, e.g., other fluorescent proteins (FPs), or other exogenous proteins or molecules, such as recombinases and antibiotics, may be used as a switch or as both a reporter and a switch for the control of synthetic (non-native) transcription systems. In one embodiment, an endogenous molecule may be employed, e.g., RNA, protein or lipid, as a switch or as both a reporter and a switch for the control of transcription.

Thus, the invention provides a detection system for a target molecule comprising: a first fusion protein comprising a DNA binding protein or a portion thereof linked to a first binding protein for the target molecule; and a second fusion protein comprising a transcriptional activator or repressor protein or a portion thereof linked to a second binding protein for the target molecule. In one embodiment, the first binding protein and the second binding protein bind to different epitopes of the target molecule.

Other fusion proteins are also envisioned. For example, a first fusion protein may comprise a first portion of a selected native protein with a detectable activity linked to a first binding protein for a target molecule and a second fusion protein may comprise a second portion of the selected protein linked to a second binding protein for the target molecule, wherein the first and second portions together reconstitute a protein with an activity of the selected protein, e.g., binding a specific nucleic acid sequence. In one embodiment, the selected protein is a recombinase.

In another embodiment, a first fusion protein may comprise a first selected protein or a portion thereof linked to a first binding protein for a target molecule and a second fusion protein may comprise a second selected protein or portion thereof linked to a second binding protein for the target molecule. In one embodiment, the first and second selected proteins together reconstitute a protein with a detectable activity. In one embodiment, the first and second selected proteins are signaling proteins in the same pathway, e.g., the TGF-beta signaling pathway. For example, one of the selected protein may be the cytoplasmic domain for the TGF-beta receptor and the other selected protein may be the cytoplasmic domain of a receptor regulated SMAD.

The invention provides a detection system for a target molecule. The system includes a first fusion protein comprising a first binding protein for the target molecule, a transmembrane spanning domain and a first cytoplasmic domain; and a second fusion protein comprising a second binding protein for the target molecule, a transmembrane spanning domain and a second cytoplasmic domain, wherein the first and second cytoplasmic domains together reconstitute a protein with an activity. In one embodiment, a first fusion protein may comprise a first binding protein for a target molecule linked to a first polypeptide having a transmembrane domain and a first cytoplasmic domain and a second fusion protein may comprise a second binding protein for the target molecule linked to a second polypeptide having a transmembrane domain and a second cytoplasmic domain linked via a protease recognition site to a transcriptional regulatory molecule. The first and second cytoplasmic domains together reconstitute a protein with an activity, e.g., a protease that cleaves the protease recognition site.

The invention also provides a detection system for an optically detectable molecule. In one embodiment, the system includes a first fusion protein comprising a DNA binding protein or a portion thereof linked to a first binding protein for the optically detectable molecule; and a second fusion protein comprising a transcriptional activator or repressor protein or a portion thereof linked to a second binding protein for the optically detectable molecule. In one embodiment, the first binding protein and the second binding protein bind to different epitopes of the optically detectable molecule. In one embodiment, the optically detectable molecule is a fluorescent protein.

Further provided is a transgenic multicellular organism, including a transgenic *Drosophila*, zebrafish or mammal. In one embodiment, at least some of the cells of a transgenic multicellular organism, including a transgenic *Drosophila*, zebrafish or mammal comprise at least two of the following: a first fusion protein comprising a DNA binding protein or a portion thereof linked to a first binding protein for a target molecule; a second fusion protein comprising a transcriptional activator or repressor protein or a portion thereof linked to a second binding protein for the target molecule; or a nucleic acid sequence which specifically binds the DNA binding protein or portion thereof which is operably linked to a nucleic acid segment of interest. In one embodiment, the first binding protein and the second binding protein bind to different epitopes of the target molecule. In one embodiment, the transgenic mammal is a transgenic rodent, e.g., a mouse, rat, ferret, guinea pig, or rabbit, transgenic canine, transgenic feline, transgenic ovine, transgenic porcine, transgenic bovine, transgenic equine, or non-human transgenic primate. In one embodiment, the transgenic organism is prepared by crossing (breeding) organisms with a subset of the components above.

In one embodiment, the invention provides a non-human transgenic mammal comprising at least two of: a first fusion protein comprising a DNA binding protein or a portion thereof linked to a first binding protein for a target molecule; a nucleic acid sequence which specifically binds the DNA binding protein or portion thereof which is operably linked to a nucleic acid segment of interest; or a second fusion protein comprising a transcriptional activator or repressor protein or a portion thereof linked to a second binding protein for the target molecule. For example, the first ligand binding protein and the second ligand binding protein bind to different epitopes of the target molecule. In one embodiment, the target molecule is an optically detectable protein, e.g., the target molecule is an optically detectable molecule encoded by a polynucleotide segment. In one embodiment, the polynucleotide segment is in the genome of the transgenic mammal. The polynucleotide segment may be operably linked to a tissue-specific promoter.

Also provided is a transgenic multicellular organism, e.g., a transgenic vertebrate such as a mammal, at least some of the cells of which comprise at least two of the following: a first fusion protein comprising a DNA binding protein or a portion thereof linked to a first binding protein for an optically detectable molecule; a second fusion protein comprising a transcriptional activator or repressor protein or a portion thereof linked to a second binding protein molecule for the optically detectable molecule, wherein the first binding protein and the second binding protein bind to different epitopes of the optically detectable molecule; and a nucleic acid sequence which specifically binds the DNA binding protein or portion thereof which is operably linked to a nucleic acid segment of interest. In one embodiment, a transgenic mammal is a transgenic rodent, e.g., a mouse, rat, ferret, guinea pig, or rabbit, transgenic canine, transgenic feline, transgenic ovine, transgenic porcine, transgenic bovine, transgenic equine, or non-human transgenic primate. In one embodiment, the transgenic organism is prepared by crossing organisms with a subset of the components above.

Also provided is a transgenic multicellular organism comprising a first expression cassette comprising an open reading frame for a target protein. The transgenic mammal also has at least two of the following: a second expression cassette encoding a first fusion protein comprising a DNA binding protein or a portion thereof linked to a first binding protein for the target protein; a third expression cassette encoding a second fusion protein comprising a transcriptional activator or repressor protein or a portion thereof linked to a second binding protein for the target protein; and a nucleic acid sequence which specifically binds the DNA binding protein or portion thereof which is operably linked to a nucleic acid segment of interest. In one embodiment, the first binding protein and the second binding protein bind to different epitopes of the target protein. In one embodiment, the transgenic organism is prepared by crossing organisms with a subset of the components above. In one embodiment, the target molecule is an optically detectable protein.

Also provided is a transgenic multicellular organism comprising a first expression cassette comprising an open reading frame for an optically detectable protein. The transgenic organism also has at least two of the following: a second expression cassette encoding a first fusion protein comprising a DNA binding protein or a portion thereof linked to a first binding protein for an optically detectable protein; a third expression cassette encoding a second fusion protein comprising a transcriptional activator or repressor protein or a portion thereof linked to a second binding protein for the optically detectable protein; and a nucleic acid sequence which specifically binds the DNA binding protein or portion thereof which is operably linked to a nucleic acid segment of interest. In one embodiment, the first binding protein and the second binding protein bind to different epitopes of the optically detectable protein. In one embodiment, the transgenic organism is prepared by crossing organisms with a subset of the components above.

In one embodiment, the invention provides a non-human transgenic mammal comprising: a first fusion protein comprising a first portion of a selected protein linked to a first binding protein for a target molecule; the target molecule; and a second fusion protein comprising a second portion of the selected protein linked to a second binding protein for the target molecule, wherein the first and second portions together reconstitute a protein with an activity of the selected protein that includes binding a specific nucleic acid sequence.

In one embodiment, the invention provides a non-human transgenic mammal comprising a first expression cassette comprising an open reading frame for a target protein; a second expression cassette encoding a first fusion protein comprising a first portion of a selected protein linked to a first binding protein for an target molecule; and a third expression cassette encoding a second fusion protein comprising a second portion of the selected protein linked to a second binding protein for the target molecule, wherein the first and second portions together reconstitute a protein with an activity of the selected protein that includes binding a specific nucleic acid sequence.

The invention also provides a method which includes providing a non-human transgenic organism, e.g., a non-human mammal or non-vertebrate, or cells having an expression cassette expressing a target protein and optionally having an expression cassette comprising a nucleic acid sequence which specifically binds a DNA binding protein or portion thereof which is operably linked to a nucleic acid segment of interest. One or more expression cassettes encoding two different fusion proteins are introduced to the mammal or cells thereof. A first fusion protein comprises a DNA binding protein or a portion thereof linked to a first binding protein for the target protein, and a second fusion protein comprises a transcriptional activator or repressor protein or a portion thereof linked to a second binding protein for the target protein. The presence or amount or location of the target protein, or the expression of the nucleic acid segment of interest, in the mammal or cells thereof is detected. In one embodiment, the mammal or the mammalian cells comprise a second expression cassette comprising the nucleic acid sequence which specifically binds the DNA binding protein or portion thereof. In one embodiment, the mammal or the mammalian cells comprise a second expression cassette and the second expression cassette is introduced into the mammal or cells concurrently with the one or more expression cassettes encoding the two different fusion proteins. In one embodiment, the genome of the mammal or mammalian cells comprises a second expression cassette.

The invention provides a method which includes providing a non-human transgenic mammal or cells having an expression cassette expressing an optically detectable protein and optionally having an expression cassette comprising a nucleic acid sequence which specifically binds a DNA binding protein or portion thereof which is operably linked to a nucleic acid segment of interest. One or more expression cassettes encoding two different fusion proteins are introduced to the mammal or cells thereof. A first fusion protein comprises a DNA binding protein or a portion thereof linked to a first binding protein for the optically detectable protein, and a second fusion protein comprises a transcriptional activator or repressor protein or a portion thereof linked to a second binding protein for the optically detectable protein. The presence or amount or location of the optically detectable protein, or the expression of the nucleic acid segment of interest, in the mammal or cells thereof is detected.

Also provided is a method comprising detecting the presence or amount or location of a target protein or detecting the expression of a nucleic acid segment of interest in a transgenic non-human mammal or cells. The transgenic mammal or cells comprise an expression cassette expressing the target protein, an expression cassette comprising a nucleic acid sequence which specifically binds a DNA binding protein or portion thereof which is operably linked to the nucleic acid segment of interest, and one or more expression cassettes encoding two different fusion proteins, wherein a first fusion protein comprises the DNA binding protein or a portion thereof linked to a first binding protein for the target protein, a second fusion protein comprising a transcriptional activator or repressor protein or a portion thereof linked to a second binding protein for the target protein.

In one embodiment, the invention provides a method comprising detecting the presence or amount or location of an optically detectable protein or detecting the expression of a nucleic acid segment of interest in a transgenic non-human mammal or cells. The transgenic mammal or cells comprise an expression cassette expressing the optically detectable protein, an expression cassette comprising a nucleic acid sequence which specifically binds a DNA binding protein or portion thereof which is operably linked to the nucleic acid segment of interest, and one or more expression cassettes encoding two different fusion proteins, wherein a first fusion protein comprises the DNA binding protein or a portion thereof linked to a first binding protein for the optically detectable protein, a second fusion protein comprising a transcriptional activator or repressor protein or a portion thereof linked to a second binding protein for the optically detectable protein.

The invention also provides kits comprising two or more of the following: a vector comprising an open reading frame for a target protein; a vector comprising a nucleic acid sequence which specifically binds a DNA binding protein or portion thereof; a vector comprising an open reading frame for a first fusion protein comprising a DNA binding protein or a portion thereof linked to a first binding protein for the target protein; and a vector comprising an open reading frame for a second fusion protein comprising a transcriptional activator or repressor protein or a portion thereof linked to a second binding protein for the target protein. Kits having vectors encoding other fusion proteins, such as those described herein, are also provided.

The invention also provides kits comprising two or more of the following: a vector comprising an open reading frame for an optically detectable protein; a vector comprising a nucleic acid sequence which specifically binds a DNA binding protein or portion thereof; a vector comprising an open reading frame for a first fusion protein comprising a DNA binding protein or a portion thereof linked to a first binding protein for the optically detectable protein; and a vector comprising an open reading frame for a second fusion protein comprising a transcriptional activator or repressor protein or a portion thereof linked to a second binding protein for the optically detectable protein.

Vectors useful to introduce the expression cassettes encoding fusion proteins to cells include viral vectors. Vectors may be introduced to cells via any means including but not limited to electroporation and nanoparticles.

In one embodiment, the vectors of the invention provide for a first fusion protein comprising a first protein or a portion thereof linked to a first protein linker linked to a first binding protein for a target molecule; and a second fusion protein comprising a second protein or a portion thereof linked to a second protein linker linked to a second binding protein for the target molecule, wherein in the presence of the target molecule the first protein or portion thereof interacts with the second protein or portion thereof and catalyzes a reaction. In one embodiment, the target molecule is an optically detectable protein. In one embodiment, the protein linkers provide for or enhance the interaction between the first protein or portion thereof and the second protein or a portion thereof, e.g., the interaction is enhanced relative to corresponding fusion proteins without the protein linkers. In one embodiment, the linkers enhance the activity of the resulting complex of fusion proteins that are brought into proximity with the target molecule. Protein linkers may contain any primary amino acid sequence so long as the linkers enhance the activity of the resulting complex of fusion proteins that are brought into proximity with the target molecule. In one embodiment, the linkers each include intein sequences, including one linker that is from about 10 to 184 amino acids in length, or any integer between 10 and 184. In one embodiment, the two portions, in the presence of the target molecule, reconstitute the activity of a full length protein from which the portions were derived, e.g., the activity of a recombinase, a toxic protein, e.g., sarsin, an endonuclease, e.g., transcription activator-like effector nuclease (TALEN) or Cas protein (e.g., Cas nucleases, helicases, polymerases and/or nucleotide binding proteins). For example, a DNA binding domain of an endonuclease is present in one fusion protein and a nuclease domain of that endonuclease is present in another fusion protein. In one embodiment, the two proteins, in the presence of a target molecule, provide for a catalytic reaction, e.g., a TEV protease present in one fusion protein cleaves a TEV protease protein substrate in another fusion protein. In one embodiment, the reconstituted protein may target genomic loci for alteration. In one embodiment, expression of at least one of the following is cell- or lineage-specific: the target molecule, the first fusion protein or the second fusion protein.

The above-described vectors may be employed in cells or in various transgenic organisms as also described above. For example, in one embodiment, a transgenic mouse line contains one or more LoxP-based alleles. As disclosed hereinbelow, in the mouse retina, GFP-dependent Cre recombinase induced loxP recombination in a GFP-specific manner, making it possible to perturb development processes and conduct lineage tracing of GFP-expressed cells. A GFP-dependent Cre recombinase simplifies the means by which one can access these tools for experimentation in the mouse (or other organisms with LoxP-based alleles), given the availability of a large number of loxP-based genetic tools. A GFP-inducible Cre recombinase can be used to induce DNA recombination events only in GFP-expressing cells, expanding the repertoire of GFP-regulatable activities and the uses of transgenic GFP lines.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 13. Schematic of CRE-DOG, a GFP-dependent Cre-recombinase.

FIG. 14. GFP-dependent activation of a floxed luciferase reporter in 293T cells. N-CreintG=N-Cre-intein-GBP fusion. C-CreintG=C-Cre-intein-GBP fusion. DNA plasmids encoding GFP, CRE-DOG, and a floxed luciferase reporter were transfected into 293T cells which were assayed 24 hours later.

FIG. 15. CRE-DOG can induce recombination of reporter in response to GFP, YFP and CFP, but not dsRed, mCherry and tdTomato. DNA plasmids encoding GFP, CRE-DOG, and a floxed luciferase reporter were transfected into 293T cells, which were assayed 24 hours later.

FIG. 16. Intein domains play a role in the GFP-dependency of recombinase activity. Different fusion constructs bearing split-Cre fragments fused either directly to intein and GBP (N-CreintG and C-CreintG), or GBP only (N-CreG and C-CreG), indicate that both intein components play a role in conferring the fusion constructs with GFP-dependent recombination activity. The luciferase assay was performed in transfected 293T cells.

FIG. 17. CRE-DOG induces GFP-dependent recombination in the mouse retina. A.) Schematic of experiment. B.) CAG-GFP C.) Rho-GFP D.) mGluR6-GFP. Electroporation of DNA plasmids encoding CRE-DOG components into the mouse retina, which was assayed 14 days post-natal birth.

DETAILED DESCRIPTION

Figure 1:
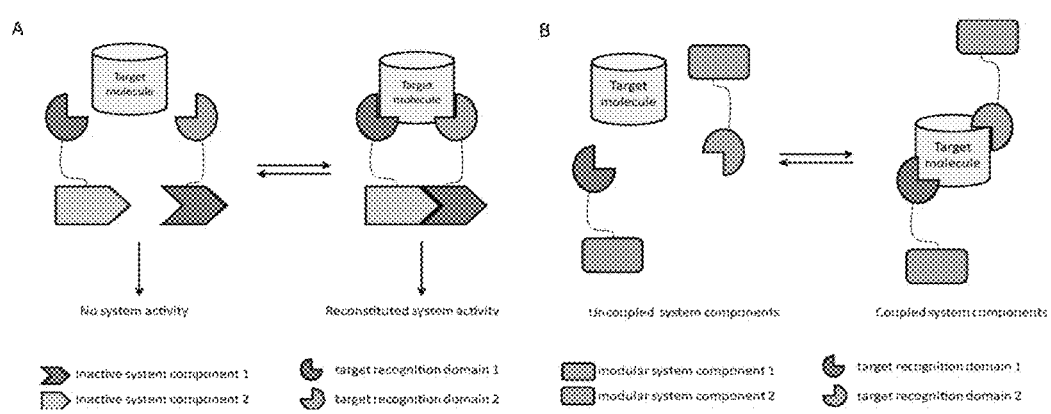
FIG. 1. A GFP-detecting transcription system. A) Synthetic devices can be designed such that their desired activities are dependent on the presence of a target molecule. Fusion proteins containing the target molecule recognition domain and either the modular device components (A) or the inactive device components. (B) are used to detect the target. C) Concept of a GFP-dependent transcription device (GDTD). Sequence-specific DNA binding domain (DBD) and transcriptional activation domain (AD) are separately fused to GFP binding proteins (GBPs) differing in their recognition epitope on GFP. When GFP is present, a DBD-GFP-AD complex is formed, resulting in transcription of genes downstream of the UAS promoter. D) Plasmids encoding different combinations of GFP, DBD, AD were transfected with UAS-luc2 and pRen into 293T cells and 24 hours later assayed for luciferase activity. GBP1-VP16AD can localize GFP to the nucleus in 293T cells, but it cannot do so for GFPmGBP1 (image in E). F) Specificity of GDTDs for different FPs. GFP and its derivatives, CFP and YFP, can all induce strong luciferase activity in the presence of GDTD2/7. CFP induce GDTD1/6 activity at a lower level, $p<0.001$, $n=9$. Scale bar is 10 µm. G) Dosage response curve of GDTDs to GFP. Varying molar ratios of GFP:GDTD plasmids (x-axis) were transfected into 293T cells along with a UAS luciferase reporter. H) Reversibility and reinduction of GDTD activity. 293T cells transfected with TRE-GFP or TRE-GFPd2, GDTD1/6, CAG-rtTA, UAS luc2 and pRen incubated with or without 0.1 µg/mL doxycycline for 16 hr. Media change into (+) or out of (−) doxycycline occurred at 0, 16, and 40 hours post-transfection.

The green fluorescent protein (GFP) is commonly used to visualize specific cell types and proteins, e.g., to visualize specific cell types in transgenic animals. A system is described herein that makes target molecules, e.g., optically detectable molecules such as GFP, as well as other molecules as described herein, useful for labeling and/or regulating biological activities. The system controls transcription, e.g., only in the presence of the optically detectable molecule, and is highly modular; it can be easily adjusted for DNA binding specificity, transcriptional potency, and drug-inducibility, which can be correlated to target molecule properties, such as fluorescence intensity and nuclear localization for GFP and GBP fused to domains that translocate to the nucleus. For example, transcription was modulated in vivo in a GFP-dependent manner in transgenic GFP mouse lines. Thus, target molecules may be employed as a switch in synthetic biological circuits and have the potential to co-opt unmodified genomic products for artificial purposes.

The invention provides a system to control transcription in vitro or in vivo. In one embodiment, the system includes a first vector comprising an open reading frame for a first fusion protein, or the first fusion protein; a second vector comprising an open reading frame for a second fusion protein, or the second fusion protein; a third vector comprising an open reading frame for a target molecule (a reporter) such as a FP, or the target molecule; and a nucleic acid sequence that binds a specific DNA binding protein or a portion thereof, operably linked to an open reading frame of interest. In one embodiment, a cell, e.g., a mammalian cell, comprises the first vector, the second vector, the third vector, or the nucleic acid sequence that binds a specific DNA binding protein or a portion thereof, operably linked to an open reading frame of interest, or any combination thereof. In one embodiment, the genome of the cell comprises a fourth vector comprising the nucleic acid sequence that binds a specific DNA binding protein or a portion thereof. In one embodiment, a cell comprises the first vector, the second vector, the nucleic acid sequence that binds a specific DNA binding protein or a portion thereof, operably linked to an open reading frame of interest, and the reporter molecule, for instance, a fluorophore, that is introduced to the cell. In one embodiment, the reporter molecule comprises a heterologous nuclear localization peptide sequence.

In one embodiment, the first vector comprises an open reading frame for a first fusion protein comprising a DNA binding protein, or a portion thereof, fused to a first reporter molecule binding protein, or a portion thereof. In one embodiment, the DNA binding protein, or a portion thereof, is N-terminal to the reporter molecule binding protein, or portion thereof. In one embodiment, the DNA binding protein, or a portion thereof, is C-terminal to the reporter molecule binding protein, or portion thereof.

Exemplary DNA binding proteins include, but are not limited to transcription factors, Gal4, hypoxia inducible factor (HIF), e.g., HIF1α, cyclic AMP response element binding (CREB) protein, LexA, rtTA, endonucleases, zinc finger binding domains, transcription activator like effectors (TALE) domains, or synthetic DNA binding domains, e.g., LTPEQVVAIASNIGGKQALEVTVQRLLPVLLQAHG (SEQ ID NO:2) (see Boch et al., 2011).

Exemplary reporter proteins include, but are not limited to, FPs, e.g., GFP, red FP, cyan FP or yellow FP, luciferase, beta-galactosidase, beta-glucuronidase, β-lactamase, alkaline phosphatase, or peroxidase. In one embodiment, the reporter protein is not a hydrolytic enzyme.

Exemplary reporter molecules may include fluorophores including but are not limited to a xanthene, coumarin, chromene, indole, isoindole, oxazole, BODIPY, a BODIPY derivative, imidazole, pyrimidine, thiophene, pyrene, benzopyrene, benzofuran, fluorescein, rhodamine, rhodol, phenalenone, acridinone, resorufin, naphthalene, anthracene, acridinium, α-napthol, β-napthol, dansyl, cyanines, oxazines, nitrobenzoxazole (NBD), dapoxyl, naphthalene imides, styryls, and the like.

In one embodiment, the target molecule binding protein is an antibody or a portion thereof, e.g., a scFV or a single domain antibody (sdAb) that is based on the recombinant variable heavy domains from the heavy chain only antibodies found in Camelids and sharks. Other binding proteins include intrabodies such as those in Olson and Roberts (2007), the disclosure of which is incorporated by reference herein.

Optionally, the first fusion protein further comprises a ligand binding domain, e.g., one that binds an anthracycline such as doxycyline, tetracycline or an estrogen, e.g., 11β-(4-dimethylaminophenyl)-17β-hydroxy-17α-propinyl-4,9-estradiene-3-one; 11β-(4-dimethylaminophenyl)-17α-hydroxy-17β-(3-hydroxypropyl)-13α-methyl-4,9-gonadiene-3-one; 11β-(4-acetylphenyl)-17β-hydroxy-17α-(1-propinyl)-4,9-estradiene-3-one; 11β-(4-dimethylaminophenyl)-17β-hydroxy-17α-(3-hydroxy-1(Z)-propenyl-estra-4,9-diene-3-one; (7β,11β, 17β)11-(4-dimethylaminophenyl)-7-methyl-4',5'-dihydrospiro[ester-4,9-diene-17,2'(3'H)-furan]-3-one; (11β, 14β,17α)-4',5'-dihydro-11-(4-dimethylaminophenyl)[spiroestra-4,9-diene-17,2' (3'H)-furan]-3-one; or 5-alpha-pregnane-3,2-dione.

In one embodiment, the second vector comprises an open reading frame for a second fusion protein comprising a transcriptional regulatory protein, or a portion thereof, fused to a target molecule, e.g., a reporter molecule, binding protein, or a portion thereof. The second target molecule binding protein or portion thereof binds to a distinct epitope of the target molecule relative to the first target molecule binding protein. In one embodiment, the transcriptional regulatory protein, or a portion thereof, is C-terminal to the target molecule binding protein, or portion thereof. In one embodiment, the transcriptional regulatory protein, or a portion thereof, is N-terminal to the target molecule binding protein, or portion thereof. In one embodiment, the transcriptional regulatory protein is a transcriptional activator protein. In one embodiment, the transcriptional regulatory protein is a transcriptional repressor protein.

Exemplary activation domains include but are not limited to those from VP16, TA2, VP64 (a tetrameric repeat of the minimal activation domain of VP16), signal transducer and activator of transcription 6 (STATE), reticuloendotheliosis virus A oncogene (relA), TATA binding protein associated factor-1 (TAF-1), TATA binding protein associated factor-2 (TAF-2), glucocorticoid receptor TAU-1, or glucocorticoid receptor TAU-2.

Exemplary repressor domains include but are not limited to those from ETS repressor factor, the ETS repressor factor repressor domain (ERD), Kruppel-associated box (KRAB), human MAD1 protein, mSin3 interaction domain of the human MAD1 protein (SID), histone deacetylase, DNA methylase, or is a derivative or multimer of KRAB, SID, or ERD selected from the group consisting of KRAB-ERD, SID-ERD, $(KRAB)_2$, $(KRAB)_3$, KRAB-A, $(KRAB-A)_2$, $(SID)_2$, (KRAB-A)-SID, or SID-KRAB-A.

In one embodiment, the invention provides a detection system for a target molecule comprising: a first fusion protein comprising a DNA binding protein or a portion thereof linked to a first binding protein for the target molecule; and a second fusion protein comprising a transcriptional activator or repressor protein or a portion thereof linked to a second binding protein for the target molecule. In one embodiment, the first binding protein and the second binding protein bind to the same epitopes of the target molecule. For example, the target molecule may have a repeated epitope or may be a multimer. In one embodiment, the first binding protein and the second binding protein bind to different epitopes of the target molecule. In one embodiment, the fusion proteins are in a cell, e.g., the cell comprises a nucleic acid sequence which specifically binds the DNA binding protein or portion thereof operably linked to a nucleic acid segment of interest. In one embodiment, the target molecule is a fluorescent protein. In one embodiment, the first binding protein, the second binding protein or both, are antibodies or portions thereof.

Further provided is a non-human transgenic mammal, the cells of which include at least two of the following: a first fusion protein comprising a DNA binding protein or a portion thereof linked to a first binding protein for a target molecule; a second fusion protein comprising a transcriptional activator or repressor protein or a portion thereof linked to a second binding protein for the target molecule; and a nucleic acid sequence which specifically binds the DNA binding protein or portion thereof which is operably linked to a nucleic acid segment of interest. In one embodiment, the first binding protein and the second binding protein bind to different epitopes of the target molecule. In one embodiment, the target molecule is an optically detectable protein, and for example, the cells of the transgenic mammal comprise an expression cassette comprising an open reading frame for the optically detectable protein.

In another embodiment, the invention provides a non-human transgenic mammal comprising a first expression cassette comprising an open reading frame for a target molecule and at least two of the following: a second expression cassette encoding a first fusion protein comprising a DNA binding protein or a portion thereof linked to a first binding protein for a target molecule; a third expression cassette encoding a second fusion protein comprising a transcriptional activator or repressor protein or a portion thereof linked to a second binding protein for the target molecule and a nucleic acid sequence which specifically binds the DNA binding protein or portion thereof which is operably linked to a nucleic acid segment of interest. In one embodiment, the first binding protein and the second binding protein bind to different epitopes of the target molecule.

Also provided is a method of using a non-human transgenic mammal or cells thereof having an expression cassette expressing a target protein, e.g., an optically detectable protein, and optionally having an expression cassette comprising a nucleic acid sequence which specifically binds a DNA binding protein or portion thereof which is operably linked to a nucleic acid segment of interest. The method includes introducing to the mammal or cells thereof one or more expression cassettes encoding two different fusion proteins, wherein a first fusion protein comprises a DNA binding protein or a portion thereof linked to a first binding protein for the target protein, a second fusion protein comprising a transcriptional activator or repressor protein or a portion thereof linked to a second binding protein for the target protein; and detecting the presence or amount or location of the target protein or detecting the expression of the nucleic acid segment of interest in the mammal or cells thereof. In one embodiment, the mammal or cells thereof comprise the expression cassette comprising the nucleic acid sequence which specifically binds the DNA binding protein or portion thereof. In one embodiment, the expression cassette comprising the nucleic acid sequence which specifically binds the DNA binding protein or portion thereof is introduced into the mammal or cells thereof concurrently with the one or more expression cassettes encoding the two different fusion proteins.

Exemplary Systems and Methods

In one embodiment, the invention provides a detection system for a target molecule The system includes a first fusion protein comprising a first protein or a portion thereof linked to a first protein linker linked to a first binding protein for the target molecule; and a second fusion protein comprising a second protein or a portion thereof linked to a second protein linker linked to a second binding protein for the target molecule, wherein in the presence of the target molecule the first protein or portion thereof interacts with the second protein or portion thereof and catalyzes a reaction. In one embodiment, the first binding protein and the second binding protein bind to different epitopes of the target molecule. In one embodiment, the fusion proteins are in a cell. In one embodiment, the cell comprises a nucleic acid sequence which specifically binds the DNA binding protein or portion thereof operably linked to a nucleic acid segment of interest. In one embodiment, the target molecule is a native protein. In one embodiment, the target molecule is a heterologous protein, e.g., a fluorescent protein. In one embodiment, the first binding protein, the second binding protein or both, are antibodies or portions thereof. In one embodiment, the system further comprises the target molecule. In one embodiment, the first protein or portion thereof is a DNA binding protein and the second protein or portion thereof is a transcriptional activator or repressor protein or a nuclease. In one embodiment, the first protein or portion thereof is a protease and the second protein or portion thereof is substrate for the protease. In one embodiment, the first protein or portion thereof is a portion of a recombinase, toxic protein, protease, beta-galactoside, beta-lactamase, luciferase, dihydrofolate reductase, thymidine kinase or chorismate mutase. In one embodiment, the first portion is a DNA binding domain of a protein and the second portion is a nuclease domain of a protein. In one embodiment, the DNA binding protein is GAL4, TALE, Cas, LexA or rtTA3G, or a portion thereof, or binds an anthracycline. In one embodiment, the transcription activator is VP16 or p65, or a portion thereof. In one embodiment, the first fusion protein has multiple copies of the first protein or portion thereof. In one embodiment, the second fusion protein has multiple copies of the second protein, or portion thereof. In one embodiment, the target molecule is a multimer.

The invention also provides a detection system for a target molecule which includes a first fusion protein comprising a first portion of a selected first protein linked to a first binding protein for the target molecule; and a second fusion protein comprising a second portion of the selected second protein linked to a second binding protein for the target molecule, wherein the first and second portions together reconstitute a protein with an activity of the full-length protein. In one embodiment, the first and second selected proteins are the same. In one embodiment, the portions together reconstitute a protein that binds a specific nucleic sequence. In one embodiment, the first binding protein and the second binding protein bind to different epitopes of the target molecule. In one embodiment, the reconstituted protein is a recombinase. In one embodiment, the first fusion protein further comprises a first protein linker between the first portion of the selected first protein and the first binding protein for the target molecule, and the second fusion protein further comprises a second protein linker between the portion of the selected second protein and the second binding protein for the target molecule, wherein the first and second linkers interact and in the presence of the target molecule have an enhanced interaction relative to fusion proteins that lack the protein linkers. For example, the first and second proteins together reconstitute a protein that is an enzyme, e.g., a protease, beta-galactoside, a recombinase, beta-lactamase, luciferase, dihydrofolate reductase, thymidine kinase or chorismate mutase. In one embodiment, the first and second proteins together reconstitute a fluorescent protein. In one embodiment, the first and second protein linkers are portions of an intein.

The invention also provides a non-human transgenic mammal, comprising: a first fusion protein comprising a first protein or a portion thereof linked to a first protein linker linked to a first binding protein for a target molecule; and a second fusion protein comprising a second protein or a portion thereof linked to a second protein linker linked to a second binding protein for the target molecule, wherein in the presence of the target molecule the first protein or portion thereof interacts with the second protein or portion thereof and catalyzes a reaction. In one embodiment, the first binding protein and the second binding protein bind to different epitopes of the target molecule. In one embodiment, the target molecule is an optically detectable molecule encoded by a polynucleotide segment. In one embodiment, the polynucleotide segment is in the genome of the transgenic mammal. In one embodiment, the polynucleotide segment is operably linked to a tissue-specific promoter.

Further provided is a non-human transgenic mammal, comprising a first expression cassette comprising an open reading frame for a target protein and at least two of the following: a second expression cassette encoding a first fusion protein comprising a first portion of a selected protein linked to first protein linker linked to a first binding protein for the target protein; a third expression cassette encoding a second fusion protein comprising a second portion of the selected protein linked to a second protein linker linked to a second binding protein for the target protein; and a nucleic acid sequence for a second target, wherein the first portion and the second portion together reconstitute an active protein, and wherein the reconstituted protein acts on the second target. In one embodiment, the first binding protein and the second binding protein bind to different epitopes of the target protein.

Also provided is a method comprising: providing a non-human transgenic mammal or mammalian cells having a first expression cassette comprising an open reading frame for a target protein and optionally having a nucleic acid segment of interest; introducing to the mammal or the mammalian cells, one or more expression cassettes encoding two different fusion proteins, wherein a first fusion protein comprises a portion of a first selected protein linked to a first protein linker linked to a first binding protein for the target protein, a second fusion protein comprises a second portion of the selected protein linked to a second linker linked to a second binding protein for the target protein, wherein the first portion and the second portion together reconstitute a protein that binds to the nucleic acid segment of interest or interacts with a gene product encoded by the nucleic acid segment of interest; and detecting the presence, amount or location of the target protein or detecting the expression of the nucleic acid segment of interest or the gene product in the mammal or the mammalian cells. In one embodiment, the mammal or the mammalian cells comprise the second expression cassette. In one embodiment, the second expression cassette is introduced into the mammal or cells concurrently with the one or more expression cassettes encoding the two different fusion proteins. In one embodiment, the genome of the mammal or mammalian cells comprises the second expression cassette. In one embodiment, the first portion and the second portion together comprise a recombinase. In one embodiment, the second expression cassette comprises recognition sites for the recombinanse.

The invention also provides a method comprising: detecting the presence or amount or location of a target protein or detecting the expression of a nucleic acid segment of interest in a transgenic non-human mammal or cells, wherein the transgenic mammal or cells comprise a first expression cassette expressing the target protein, a second expression cassette comprising a nucleic acid sequence, and one or more expression cassettes encoding two different fusion proteins, wherein a first fusion protein comprises a portion of a first selected protein linked to a first protein linker linked to a first binding protein for the target protein, a second fusion protein comprising a second portion of the selected protein linked to a protein linker linked to a second binding protein for the target protein. In one embodiment, the first expression cassette comprises a cell- or lineage-specific promoter.

The invention further provides a non-human transgenic mammal, comprising: a first fusion protein comprising a first portion of a selected protein linked to a first protein linker linked to a first binding protein for a target molecule; the target molecule; and a second fusion protein comprising a second portion of the selected protein linked to a second protein linker linked to a second binding protein for the target molecule, wherein the first and second portions together reconstitute a protein with an activity of the selected protein. In one embodiment, the activity includes binding a specific nucleic acid sequence.

Also provided is a non-human transgenic mammal, comprising a first expression cassette comprising an open reading frame for an optically detectable protein; a second expression cassette encoding a first fusion protein comprising a first portion of a selected protein linked to a first protein linker linked to a first binding protein for a target protein; and a third expression cassette encoding a second fusion protein comprising a second portion of the selected protein linked to a second protein linker linked to a second binding protein for the target protein, wherein the first and second portions together reconstitute a protein with an activity of the selected protein. In one embodiment, the activity includes that includes binding a specific nucleic acid sequence.

Further provided is a non-human transgenic mammal, comprising: a first fusion protein comprising a protein or a portion thereof linked to a first protein linker linked to a first binding protein for the target molecule; and a second fusion protein comprising a second protein or portion thereof linked to a second protein linker linked to a second binding protein for the target molecule, wherein in the presence of the target molecule the first protein or portion thereof interacts with the second protein or portion thereof and catalyzes a reaction which is enhanced relative to a corresponding reaction with fusion proteins that lack the first and second protein linkers. In one embodiment, the first ligand binding protein and the second ligand binding protein bind to different epitopes of the target molecule. In one embodiment, the target molecule is an optically detectable protein. In one embodiment, the target molecule is an optically detectable molecule encoded by a polynucleotide segment. In one embodiment, the polynucleotide segment is in the genome of the transgenic mammal. In one embodiment, the polynucleotide segment is operably linked to a tissue-specific promoter.

The invention provides a non-human transgenic mammal, comprising a first expression cassette comprising an open reading frame for a target protein; a second expression cassette encoding a first fusion protein comprising a first protein or a portion thereof linked to a first protein linker linked to a first binding protein for a target molecule; and a third expression cassette encoding a second fusion protein comprising a second protein or a portion thereof linked to a second protein linker linked to a binding protein for the target molecule, wherein in the presence of the target molecule the first protein or portion thereof interacts with the second protein or portion thereof and catalyzes a reaction which is enhanced relative to a corresponding reaction with fusion proteins that lack the first and second protein linkers. In one embodiment, the first binding protein and the second binding protein bind to different epitopes of the target molecule. In one embodiment, the target molecule is an optically detectable protein.

Further provided is a method comprising: providing a non-human transgenic mammal or mammalian cells having a first expression cassette comprising an open reading frame for a target protein and optionally having a second expression cassette comprising a nucleic acid segment of interest; introducing to the mammal or the mammalian cells, one or more expression cassettes encoding two different fusion proteins, wherein a first fusion protein comprises a first protein or a portion thereof linked to a first protein linker linked to a first binding protein for the target protein, a second fusion protein comprises a second protein or a portion thereof linked to a second protein linker linked to a second binding protein for the target protein; and detecting the presence, amount or location of the target protein, or detecting the presence or absence of expression of the nucleic acid segment of interest in the mammal or the mammalian cells, wherein in the presence of the target molecule the first protein or portion thereof interacts with the second protein or portion thereof and catalyzes a reaction which is enhanced relative to a corresponding reaction with fusion proteins that lack the first and second protein linkers. In one embodiment, the mammal or the mammalian cells comprise the second expression cassette comprising the nucleic acid sequence which specifically binds the DNA binding protein or portion thereof. In one embodiment, the second expression cassette is introduced into the mammal or cells concurrently with the one or more expression cassettes encoding the two different fusion proteins. In one embodiment, the genome of the mammal or mammalian cells comprises the second expression cassette.

Also provided is a method comprising: detecting the presence or amount or location of a target protein or detecting the expression of a nucleic acid segment of interest in a transgenic non-human mammal or cells, wherein the transgenic mammal or cells comprise a first expression cassette expressing the target protein, a second expression cassette comprising a nucleic acid segment of interest, and one or more expression cassettes encoding two different fusion proteins, wherein a first fusion protein comprises a first protein or a portion thereof linked to a first protein linker linked to a first binding protein for the target protein, a second fusion protein comprising a second protein or a portion thereof linked to a second protein linker linked to a second binding protein for the target protein, wherein in the presence of the target protein the first protein or portion thereof interacts with the second protein or portion thereof and catalyzes a reaction which is enhanced relative to a corresponding reaction with fusion proteins that lack the first and second protein linkers.

The invention will be further described by the following non-limiting examples.

Example 1

Materials and Methods

Animals.

Timed pregnant CD1 mice were obtained from Charles River Breeding Laboratories. Crx-GFP (Samson et al., 2009). TRE-Cre (Jackson laboratories). All animal experiments performed were approved by the Institutional Animal Care and Use Committee at Harvard University.

Molecular Biology

GBP Sequences.

GBP 1 and 4 sequences were obtained from published protein sequence (PDB; 3K1K for GBP1 and 3G9A for GBP4), backtranslated, codon-optimized for the mouse and synthesized by Genewiz (New Jersey), generating pUC57-GBP1 and pUC57-GBP4. Plasmids carrying GBPs 2, 5, 6 and 7 were obtained from Ulrich Rothbauer (Ludwig-Maximilians-Universität München). GBP6 was synthesized based on provided sequence to generate pUC57-GBP6 (Genewiz).

Miscellaneous Vectors.

pCAG-GFP (Addgene plasmid 11150), pCAG-YFP (Addgene plasmid 11180), pCAG-CFP (Addgene plasmid 11179), pCAG-Tdtomato, pCAG-mCherry, pCAG-DsRed (Addgene plasmid 11151), pCAG GFPd2 (Addgene plasmid 14760), pRL-TK (Promega, #E2241), pBS SK+ (Dymecki lab)

pCAG-GFPmGBP1.

To produce GFPmGBP1, splicing by overlap extension (SOE) PCR was performed to generate E142K and N146Q mutations in EGFP. The mutagenized PCR product has AgeI-kozak consensus sequence and NotI on the 5' and 3' ends, respectively. Using AgeI/NotI, this fragment was cloned in place of EGFP in the pCAG-GFP vector.

pNdrg4-GFP.

The GFP coding sequence was excised from pCAG-GFP via EcoRI/NotI restriction digest. This fragment is then cloned in place of GFPx2 in pNdrg4-GFPx2.

pUAS-Tdtomato.

Tdtomato was amplified from pCAG-Tdtomato with EcoRI and XbaI restriction sites added on the 5' and 3' ends, respectively. This fragment was cloned into pUAS-luc2 via EcoRI/XbaI, replacing the luciferase sequence to give pUAS-Tdtomato.

pTRE-Tdtomato and pTRE-luc2.

TREtight promoter was amplified from pTRE-TIGHT miR-1 (Addgene plasmid 14896), generating SphI and SbfI restriction sites on the 5' end. This fragment was cloned into pUAS Tdtomato via SphI/EcoRI restriction sites, replacing the UAS-hsp70 sequence and giving pTRE-Tdtomato. The same fragment was digested with SbfI/EcoRI and cloned into the corresponding sites in pUAS Luc2, replacing the UAS-hsp70 sequence and giving pTRE-Luc2 pLexAop2-Tdtomato and pLexAop2-Luc2.

LexAop2-hsp70 minimal promoter was amplified from pJFRC18-8XLexAop2-mCD8::GFP (Addgene plasmid 26225), generating the EcoRI restriction site on the 3' end. This PCR fragment was cloned into pUAS-Tdtomato via HindIII/EcoRI restriction sites, replacing UAS-hsp70 sequence and giving pLexAop2-Tdtomato. The same fragment was digested with SbfI/EcoRI and cloned into the corresponding sites in pUAS luc2, replacing UAS-hsp70 sequence and giving pLexAop2-Luciferase.

pUAS-Cre.

Cre recombinase was amplified from pNrl-Cre (Addgene plasmid 13780), generating an EcoRI-kozak sequence and XbaI restriction site on the 5' and 3' ends, respectively. This fragment was inserted in place of luc2 in the pUAS-luc2 vector via EcoRI/XbaI restriction sites.

pUAS-Flpe.

Flpe recombinase was amplified from pCAG-flpe (Addgene plasmid 13787), generating an EcoRI-kozak sequence and XbaI restriction site on the 5' and 3' ends, respectively. This fragment was inserted in place of luc2 in the pUAS-luc2 vector via EcoRI/XbaI restriction sites.

pTRE-GFP and pTRE-GFPd2.

GFP and GFPd2 were amplified from CAG-GFP and Hes1-GFPd2 (Addgene plasmid 14808), respectively. Both fragments were conferred EcoRI-kozak sequence and XbaI restriction site on the 5' and 3' ends, respectively. These fragments were each separately inserted in place of luc2 in the pTRE-luc2 vector via EcoRI/XbaI restriction sites.

pCAG-N-G4DBD.

The GAL4 DNA binding domain (G4DBD) was amplified from pAcPL-Gal4DBD (Addgene plasmid 15304), with AgeI-kozak consensus sequence and NheI-10Glycine-MfeI-NotI overhangs on the 5' and 3' ends, respectively. This fragment was inserted in place of EGFP in the pCAG-GFP vector via AgeI/NotI restriction sites.

pCAG-C-G4DBD.

The GAL4 DNA binding domain (G4DBD) was amplified from pAcPL-Gal4DBD (Addgene plasmid 15304), with AgeI-NheI and NotI overhangs added on the 5' and 3' ends, respectively. This fragment was inserted in place of EGFP in the pCAG-GFP vector via AgeI/NotI restriction sites.

pCAG-VP16AD.

The VP16 activation domain (VP16AD) was amplified from pAcPL-VP16 (Addgene plasmid 15305), generating AgeI-kozak consensus sequence and NotI restriction site on the 5' and 3' ends, respectively. This fragment was inserted in place of EGFP in the pCAG-GFP vector via AgeI/NotI restriction sites.

GDTD1/6 Constructs

GBP1-Containing Constructs.

In all GBP1-containing constructs, GBP1 was amplified from pUC57-GBP1 with primers bearing various overhangs on the PCR products (see Table 1).

pCAG-GBP1-10gly-G4DBD:

AgeI-koz-GBP1-NheI PCR fragment was cloned into pCAG-C-G4DBD via AgeI/NheI sites.

pCAG-G4DBD-10gly-GBP1:

NheI-10gly-MfeI-GBP1-NotI PCR fragment was cloned into pCAG-N-G4DBD via NheI/NotI sites.

pCAG-G4DBD-GBP1:

NheI-GBP1-NotI PCR fragment was cloned into pCAG-N-G4DBD via NheI/NotI sites.

pCAG-G4DBD-GBP1x2:

NheI-GBP1-NheI PCR fragment was cloned into pCAG-G4DBD-10gly-GBP1 via NheI restriction site.

pCAG-G4-DBD-10gly-GBP1x2:

NheI-10gly-SpeI-GBP1-NheI PCR fragment was cloned into pCAG-G4DBD-10gly-GBP1 via NheI restriction site.

pCAG-GBP1x2-10gly-G4DBD:

NheI-GBP1-NheI PCR fragment was cloned into pCAG-GBP1-10gly-DBD via NheI restriction site.

pCAG-VP16AD-10gly-GBP1:

NheI-10gly-MfeI-GBP1-NotI PCR fragment was cloned into pCAG-VP16AD via NheI/NotI sites.

pCAG-rtTADBD-GBP1:

The DNA binding domain of Reverse Tetracycline transactivator 3G (rtTA3G) was amplified from pLenti CMV rtTA3G Blast (R980-M38-658) (Addgene plasmid 31797). The PCR product contains AgeI-Kozak consensus sequence and NheI restriction site on the 5' and 3' ends, respectively. This fragment was cloned into pCAG-G4DBD-GBP1 via AgeI/NheI and replaces G4DBD.

pCAG-GBP1-10gly-lexADBD:

The LexA DNA binding domain (LexA DBD) was amplified from pCMV Lex VP16 HA (P#1708) (Addgene plasmid 14593) with NheI-10gly-XbaI and NotI overhangs on the 5' and 3' ends, respectively. This fragment was cloned into pCAG-GBP1-10gly-G4DBD via NheI/NotI and replaces G4DBD.

GBP6-Containing Constructs.

For all GBP6-containing constructs, GBP6 was amplified from pUC57-GBP6 with various overhangs on the PCR products.

pCAG-G4DBD-GBP6:

NheI-GBP6-NotI PCR product was cloned into pCAG-N-G4DBD via NheI/NotI restriction sites.

pCAG-VP16AD-GBP6:

NheI-GBP6-NotI PCR product was cloned into pCAG-VP16AD via NheI/NotI restriction sites pCAG-GBP6-10gly-G4DBD:

AgeI-Kozak consensus-GBP6-NheI was cloned into pCAG-C-G4DBD via AgeI/NheI sites.

pCAG-GBP6-10gly-VP16minx2, pCAG-GBP6-10gly-VP16minx3, pCAG-GBP6-10gly-VP16minx4:

The VP16minx2, x3, x4 sequences were amplified from CMV rtTA3G Blast (R980-M38-658) (Addgene plasmid 31797) with NheI-10gly-MfeI and NotI overhangs on the 5' and 3' end, respectively. Each PCR fragment was separately cloned into pCAG-GBP6-10gly-G4DBD.

pCAG-p65AD-GBP6:

The p65 activation domain (p65AD) was amplified from pCMV4 p65 (Addgene plasmid 21966) with an NLS. This fragment was then amplified again to add AgeI-Kozak consensus sequence and NheI on the 5' and 3' end, respectively. The final PCR product was then cloned into pCAG-VP16AD-GBP6 via AgeI and NheI sites, replacing VP16AD.

GDTD2/7 Constructs pCAG-GBP2-10gly-G4DBD: GBP2 was amplified from GBP2 chromobody plasmid (Kirchhofer et al 2010) with AgeI-koz and NheI sequences on the 5' and 3' ends, respectively. This fragment was cloned into pCAG-C-G4DBD via AgeI/NheI sites.

pCAG-VP16AD-10gly-GBP7:

GBP7 was amplified from GBP7 chromobody plasmid (Kirchhofer et al 2010) with NheI-10gly-MfeI on the 5' end and NotI on the 3' end. This fragment was cloned into pCAG-VP16AD via NheI/NotI sites.

Cell Culture and Transfection.

Unless stated otherwise, for all cell culture experiments, $1-2 \times 10^5$ 293T cells were seeded into 48 well plates and 1-2 days later transfected with plasmids. Plasmids were transfected via polyethyleneimine (PEI) method at a 1:4 DNA amount:PEI volume ratio. For doxycycline-inducible experiments, doxycycline hyclate (Sigma, D9891-10G) was diluted in water and used at 1 µg/mL.

Cell Culture Tdtomato Reporter Readout.

A total of 500 ng of DNA were transfected. In all experiments, 100 ng of UAS-Tdtomato, TRE-Tdtomato or LexAop-Tdtomato were included. Plasmids encoding CAG-driven XFP, GBP-DBD, GBP-VP16 and other variants were transfected at amounts adjusted for their molarity. pBS SK+ (Dymecki) or pCAG-mCherry were added to adjust the total DNA amount to equal levels. Fluorescent micrographs were taken on a Leica DMI3000B microscope with a 10× or 20× objective.

Luciferase Assay.

In all experiments, 12.5 ng UAS-luc2 (Addgene plasmid 24343) and 1.25 ng pRL-TK (Promega, (#E2241a) were included. Plasmids encoding CAG-driven XFP, GBP-DBD, GBP-VP16 and other variants were transfected at amounts adjusted for their molarity. pBS SK+ (Dymecki lab) were added to adjust the total DNA amount to 62.5 or 63.5 ng. Cells were harvested 24 hours later for Dual-luciferase assay (Promega) according to manufacturer's instructions. Lysates were pipetted into 96-well plates and read in an Analyst GT plate reader (Molecular Devices). To determine the linear range of detection for the plate reader, a standard curve was constructed by measuring luciferase activity of serial dilutions of QuantiLum recombinant luciferase (Promega). Transfection amounts were then optimized to give readings within the linear range of detection for the instrument.

In Vivo Retinal Electroporation.

P0-P2 mouse pups were electroporated as described previously (Matsuda and Cepko, 2004), except that a Femtojet Express pressure injector (Eppendorf; 920010521) delivered the DNA solution via a custom made glass needle (Origio, C060609). DNA solutions were injected at 1-1.5 µg/µL through the sclera and into the subretinal space of the mouse retina.

Ex Vivo Retinal Electroporation.

P0 Otx2 flox/Otx2 flox retinas (23) were electroporated in vitro with plasmids containing pCAG-GBP1-10gly-G4DBD (100 ng/µL), pCAG-p65AD-GBP6 (50 ng/µL), UAS-Cre (40 ng/µL), CAG-nlacZ (100 ng/µL). pCAG-GFP (100 ng/µL) or pCAG-dsRed (100 ng/µL) were used depending on the experimental conditions. In vitro electroporation was carried out as described in Emerson and Cepko (2011) except that retinas were cultured ex vivo for 8 days before harvesting.

Tetracycline Induction In Vivo.

Mothers of newborn pups were fed 0.2 mg/ml doxycycline hyclate in H20 (Sigma) from P0 to P14.

In Vivo Intraventricular Electroporation.

E14-15 mouse embryos were electroporated.

Histology.

Mouse retinas were dissected out of the eyes and fixed at room temperature for 30 minutes in 4% formaldehyde. Fixed retinas were washed in PBS and equilibrated in increasing concentration of sucrose (5/15/30%) 1×PBS pH 7.4 solution. Retinas were then equilibrated in OCT for at least 10 minutes and quickly freezed on dry ice. Retinal cryosections were cut into 20 µm slices on a Leica CM3050S cryostat (Leica Microsystems), using disposable blades.

Immunohistochemistry.

Retinal cryosections were blocked in 5% heat-inactivated normal goat serum in 0.1% TritonX-1×PBS (PBT), pH7.4 for 1 hour at room temperature and then stained with primary antibody in blocking solution overnight at 4 degrees celsius. Antibodies used in this study were: Anti-B-galactosidase (40-1a). Slides were washed in 1×PBT for three times and then incubated in secondary antibodies and DAPI for 2 hours at room temperature. Slides were then washed in 1×PBT for three times and mounted using Fluormount-G (Southern Biotechnology Associates; 0100-01).

Microscopy and Image Analysis.

Retinal sections were taken on a Zeiss LSM780 confocal microscope. Slides were scanned using a 40× oil immersion objective. Cell culture images were images were obtained on a Leica DMI3000B epifluorescence microscope. Whenever possible, images settings were adjusted for saturation. Whenever samples were to be compared within an experiment, image settings were kept constant. Occasionally, DAPI fluorescence intensity varied between slides so it was adjusted to be similar intensity between comparisons. Images were analyzed and processed on Imaris, Image J and/or Photoshop softwares.

Scale bars for Leica DMI3000B microscope was derived in the following way: actual pixel size for sample was obtained by dividing the CCD pixel size (6.45 µm×6.45 µm) by the objective magnification (10× or 20×). At 10×, the pixel size is 645 nm×645 nm. At 20× the pixel size is 322.5 nm×322.5 nm. Scale bars of specified lengths were obtained by drawing a line on Photoshop that covers the number of pixels within the specified length.

Dosage Response Curve Experiment.

A total of 100 ng total DNA were transfected. 15.5 ng of pCAG-G4DBD-GBP6 and pCAG-VP16-10lk-GBP1, 12.5 ng UAS-luc2 (Addgene plasmid 24343) and 1.25 ng pRL-TK (Promega, (#E2241a) were included. CAG-GFP plasmid was serially diluted 3 fold in water and pipetted at equal volume into transfection mixture. pCAG-mCherry plasmid was used to make up the total DNA amount. 24 hours after transfection, cells were imaged on Leica epifluorescence microscope at 20× for GFP and mCherry fluorescence before being used for Dual Luciferase Assay (Promega). All transfection conditions were repeated 3 times. Cell lysate from each repeat was split into 3 samples for luciferase assay. n=6 for each data point used for the dosage response plot. Error bars represent standard deviation.

GDTD Reversibility Experiment.

64 ng of DNA were transfected into about 50% confluent 293T cells at time 0 hr in 48 well plate. Immediately following transfection, cells were cultured in 0 μM or 0.1 μg/mL doxycycline for 16 hr. At time 16 hr, cells were exchanged into fresh media carrying 0 μM or 0.1 μg/mL doxycycline. Media change occurred again at time 32 hr. Cells were harvested at the desired time points using the passive lysis buffer (Promega) and snap froze at −80 degrees Celsius until use.

TABLE 1

Specific components of GDTDs.

| GBP combination | DBD | AD | Used in FIG. X |
| --- | --- | --- | --- |
| GAL4-based GDTD | | | |
| GBP1/6 | G4DBD-GBP6 | NLS-VP16AD-10gly-GBP1 | 1B, 1C, 1D, 1E, 1F |
| GBP1/6 | G4DBD-GBP1 | NLS-VP16AD-GBP6 | 2D, 2E |
| GBP1/6 | G4DBD-GBP1 | GBP5-10gly-VP16 min × 2 | 2D |
| GBP1/6 | G4DBD-GBP1 | GBP6-10gly-VP16 min × 3 | 2D |
| GBP1/6 | G4DBD-GBP1 | GBP6-10gly-VP16 min × 4 | 2D |
| GBP1/6 | G4DBD-GBP1 × 2 | NLS-VP16AD-GBP6 | 2D |
| GBP1/6 | G4DBD-GBP1 × 2 | GBP6-10gly-VP16 min × 2 | 2D |
| GBP1/6 | G4DBD-GBP1 × 2 | GBP6-10gly-VP16 min × 3 | 2D |
| GBP1/6 | G4DBD-GBP1 × 2 | GBP6-10gly-VP16 min × 4 | 2D |
| GBP1/6 | G4DBD-GBP1 | NLS-p65AD-GBP6 | 2E |
| GBP1/6 | G4DBD-10gly-GBP1 | NLS-p65AD-GBP6 | 2E |
| GBP1/6 | GBP1-10gly-G4DBD | NLS-p65AD-GBP6 | 3, 4 |
| GBP2/7 | GBP2-10gly-G4DBD | NLS-VP16AD-10gly-GBP7 | 1B, 1D |
| LexA-based GDTD | | | |
| GBP1/6 | GBP1-10gly-lexADBD | NLS-VP16AD-GBP6 | 2A |
| rtTA-based GDTD | | | |
| GBP1/6 | rtTADBD-GBP1 | NLS-VP16AD-GBP6 | 2B, 2C |

GDTD Screen.

A total of 6 GBPs (GBP1, 2, 4, 5, 6, 7) were used for all GDTD screens. Each GBP was fused to DBD or AD at either its N- or C-terminal end. Fusions were made with either no linker between the two protein modules, or with a 10 amino acid glycine linker. Most chimeric constructs carried a nuclear localization signal (NLS) at the N-terminal end. All chimeric constructs were placed under the control of the ubiquitous CAG promoter. The resulting CAG-chimera plasmids were combined in many possible pairs and transfected along with pCAG-GFP, UAS-luc2 and pRL-TK into 293T cells. Combinations that gave the strongest reporter induction after 24 hours were selected for further characterization.

rtTA-based GDTDs were screened similarly as above, but transfection mixtures for each DBD:AD combination were split into two culture wells, one with 1 ug/ml doxycycline and the other with no doxycycline. Functional combinations were judged to be those that gave reporter induction in the presence of doxycycline, but not in the absence of doxycycline.

AD Toxicity Screen.

Since full length VP16 AD induced a clear mispositioning of rod photoreceptors to the upper edge of the ONL, we screened for ADs that did not give this phenotype. The most useful ADs would be those that confer high transcriptional activity with minimal side effects on cellular phenotype. To determine the least toxic AD for use in the retina, selected DBD:AD combinations involving p65 or VP16min ADs were electroporated into P0 CD1 retina along with CAG-GFP, UAS-Tdt and CAG-nLacZ. Electroporation mixtures including full length GBP7:VP16 as the AD served as the control for the "toxic" phenotype, while those missing an AD served as the wildtype control. Photoreceptor mispositioning was assessed by quantifying percentage of Tdt positive cells in the upper versus lower half of the ONL.

Results

GFP is not known to be a ligand in nature, but the development of GFP binding proteins (GBPs) from Camelid antibodies (Kirchofer et al., 2010; Rothbauer et al., 2008; Rothbauer et al., 2006) have made it possible to design GFP-dependent synthetic devices. It was reasoned that GFP may be able to induce the association of modular domains and protein fragments to reconstitute useful activities such as transcription and recombination. A non-biased screen was conducted for GBP pairs that can co-occupy GFP and reconstitute a functional transcription device. It was examined whether GFP can induce the association of the GAL4 DNA binding domain (DBD) and VP16 activation domain (AD) (Sadowski et al., 1988) (FIG. 1A). DBD and AD were separately fused to GBPs in various configurations and screened pair-wise, i.e., DBD-GBP+AD-GBP combinations were screened for activation of a UAS-luciferase reporter in GFP-expressing 293T cells. Combinations involving GBP2+7 or GBP1+6 consistently gave the best reporter induction (FIG. 1B). Those two combinations were named GFP-dependent transcription devices 2/7 and 1/6 (GDTD2/7 and GDTD1/6), respectively. All subsequent GFP-dependent transcription experiments were conducted with either one of these two combinations.

The induced transcription output is dependent on all components of the system. Whereas GDTD2/7 and GDTD1/6 induced strong luciferase activity in the presence of GFP, removal of any one component from the GFP-DBD-AD transfection mixture resulted in loss of reporter induction (FIG. 1B). Similar results were obtained when a UAS-Tdtomato reporter was used in place of UAS-luciferase reporter (FIG. 1C).

Figure 5:
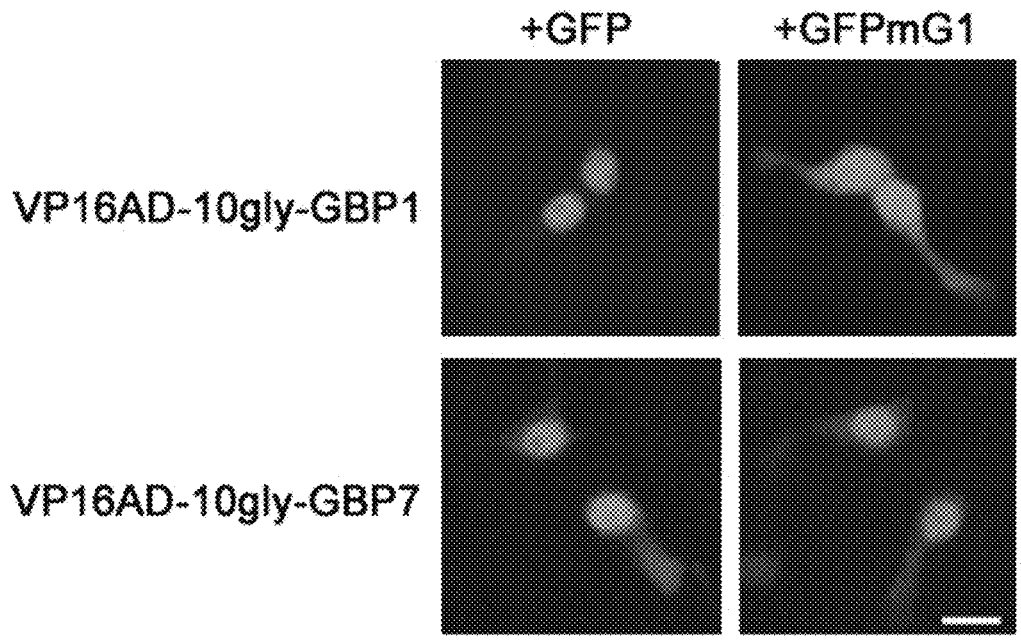
FIG. 5. VP16AD-GBP fusions can localize GFP to the nucleus. Representative images of GFP localization in 293T cells transfected with pCAG-GFP or pCAG-GFPmG1 along with VP16AD-10gly-GBP1 or VP16AD-10gly-GBP7 at a 1:2 molar plasmid ratio. Fluorescent micrographs were taken at 16 hours post-transfection. GBP1 is known to enhance fluorescence of GFP (Kirchhofer et al., 2010), so fluorescent intensity of GFP/GFPmG1 in VP16-16AD-10gly-GBP7 transfected cells were adjusted the same manner to better reveal GFP localization relative to GFP/GFPmG1 in VP16AD-10gly-GBP1 transfected cells. Scale bar is 15 µM.
Figure 6:
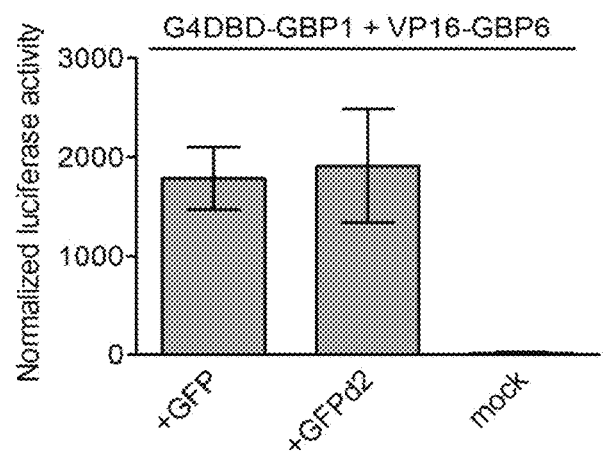
FIG. 6. Destabilized GFP can induce GDTDs to a similar extent as GFP. 293T cells were transfected with plasmids with CAG promoter driving G4DBD-GBP1 and VP16-GBP6 along with GFP, GFPd2 or control plasmid at 1.1:1:1 GFP:DBD:AD molar ratio. UAS luc2 and pRL-TK were used as the reporter and normalizing luciferase control, respectively. Cells were measured for luciferase activity 24 hours post-transfection. n=9. Error bars represent standard deviation.

Next, it was tested whether reporter induction was dependent on the ability of GBP to bind to GFP. GFP was visibly localized to the nucleus when in the presence of the nuclear-localized AD-GBP1 or AD-GBP7, consistent with their proposed interactions (FIG. 1C, FIG. 5A). GBP-DBD fusions alone do not effectively localize GFP to the nucleus (FIG. 5B). Based on the GBP1-GFP crystal structure (Kirchofer et al., 2010), GFP residues were mutated that were expected to directly interact with GBP1. Variants that retained much of their fluorescence but had reduced nuclear localization in the presence of AD-GBP1 were identified. One such variant, GFPmGBP1, carries the mutations E142K and N146Q (FIG. 1C, FIG. 5). As expected, GFPmGBP1 did not induce UAS-reporter expression in the presence of GDTD1/6 (FIG. 1B, FIG. 1C). However, GDTD2/7 responded similarly to both GFP and GFPmGBP1 (FIG. 1B). This suggests that GBP2 and GBP7 do not depend on residue 142 or 146 for binding to GFP.

The specificity of GDTD action was evaluated for GFP versus its derivatives cyano and yellow fluorescent proteins (CFP and YFP), and the Discosoma-derived red fluorescent proteins dsRed, mCherry and Tdtomato (Shaner et al., 2005). Whereas none of the red fluorescent proteins were able to induce GDTD activity, CFP and YFP induced the activation of GDTD2/7 to a similar extent as GFP (FIG. 1D). However, CFP had reduced ability to activate GDTD1/6. This is expected since CFP differs from GFP at the GBP1 interacting residue 146 (Rothbauer et al., 2008). Destabilized GFP (GFPd2) was also found to induce GDTD to a similar extent as GFP (data not shown).

In the present system, GFP is analogous to known small molecule "dimerizers" such as rapamycin, which is used as a bridging factor for synthetic proteins bearing rapamycin-binding domains found in nature (Pollock et al., 2002). Indeed, the response of GDTDs to varying GFP levels is consistent with that of other known small-molecule dimerizers (FIG. 1D) (Ho et al., 1996). GDTD activity increases linearly with GFP within a certain GFP dosage range, but increasing GFP level beyond that range leads to inhibition of GDTD activity. This inhibition effect is probably due to sequestration of GDTD components, since GFP localization in the cell correlates with GDTD activity. At limiting GFP levels, GFP is enriched in the nucleus and has a positive effect on GDTD activity. In contrast, at excessive GFP levels, GFP spreads into the cytoplasm and has a negative effect on GDTD activity (data not shown).

GDTDs are reversibly dependent on the presence of GFP. GFP was placed under the control of a tetracycline-responsive element-promoter (TRE-GFP), which is bound and activated by reverse tetracycline transactivator (rtTA) only in the presence of doxycycline. TRE-GFP induced strong luciferase activity only in the presence of both GDTDs and doxycyline. When doxycyline is removed from the culture medium, luciferase activity gradually declines, but can be re-induced by re-application of the drug (FIG. 1F). Since GFP has a long half-life (about 24 hours), it was determined whether a destabilized version of GFP (GFPd2) would make the system more reversitile. GFPd2 behaved similarly as GFP under the same conditions, except that the rate of decline in reporter activity is faster with GFPd2. It is possible that GDTDs stabilize GFPd2 by sequestering it in the nucleus and away from the degradation machinery.

Figure 2:
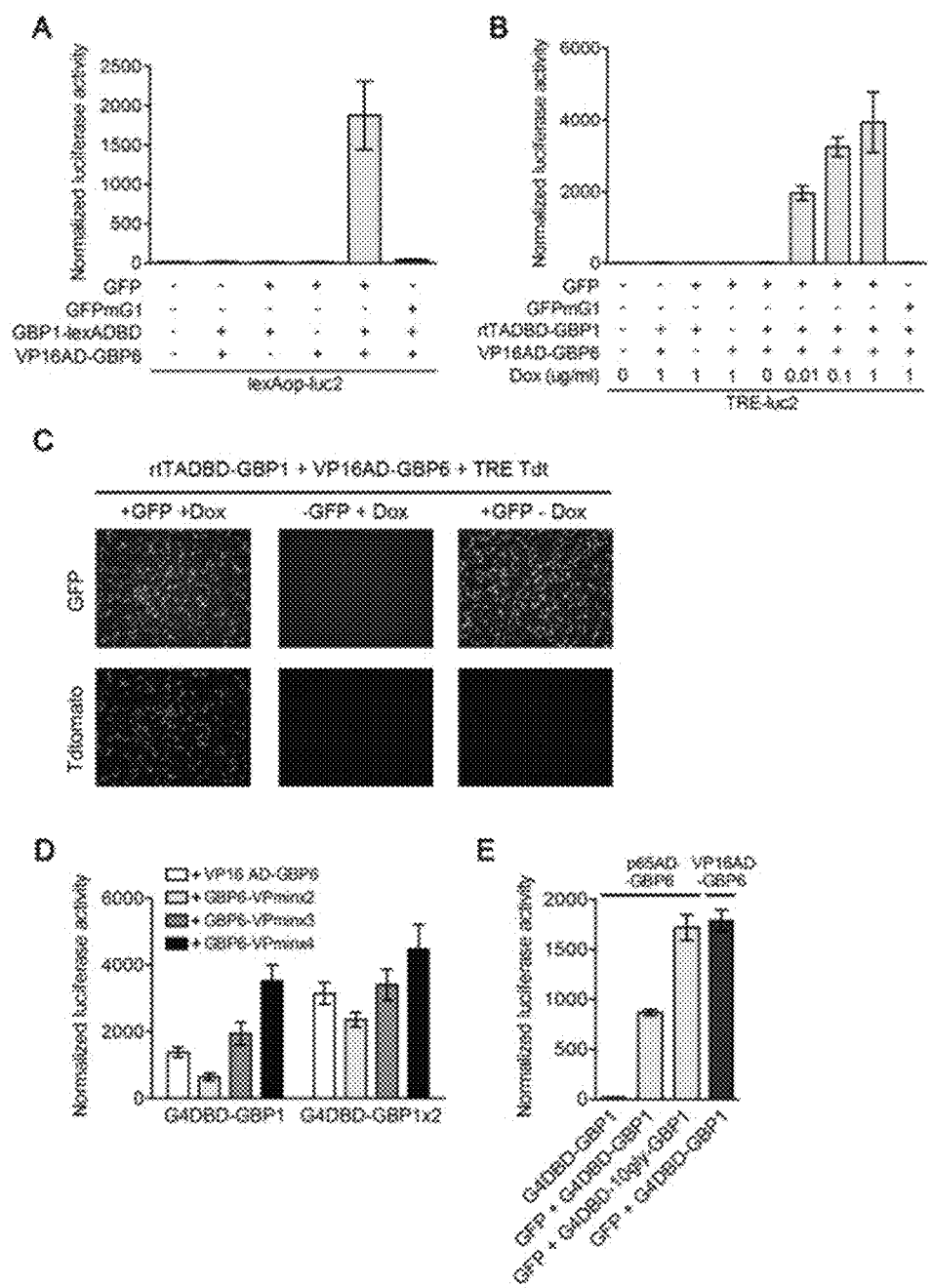
FIG. 2. The GFP-dependent transcription system is highly adjustable. In A), B), D) and E) Plasmids encoding various combinations of GFP, GFPmGI, GBP-DBD, GBP-AD, TRE/lexAop/UAS luc2 and pRL-TK were transfected into 293T cells and harvested 24 hours later for luciferase assay. In A), GBP1-lexADBD and VP16AD-GBP6 can act together to activate a lexAop-luc2 reporter only in the presence of GFP. In B), rtTADBD-GFP1 and VP16AD-GBP6 activates TRE-luc2 in a GFP and doxycycline-dependent manner. In C), experiment was performed as in B), but UAS-Tdtomato was used in place of TRE luc2 and pRL-TK. 1 ug/ml doxycycline was added in the medium. D) and E) Tuning of GDTDs with adjustable DBDs and ADs. UAS luc2 was used as the reporter.
Figure 3:
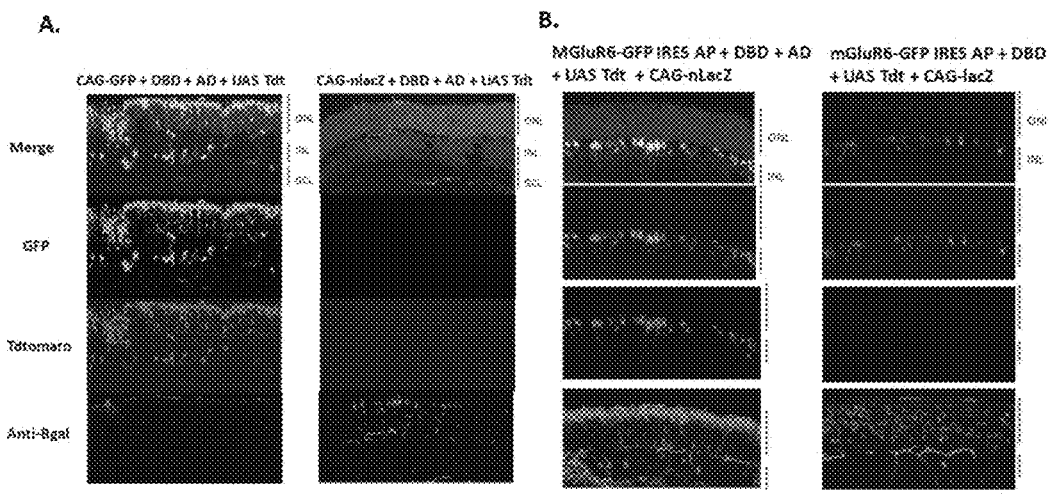
FIG. 3. GDTDs are GFP-dependent in vivo. CAG-GFP (A) or mGluR6-GFP-IRES-AP (B) were electroporated into CD1 murine retina at P0 along with GDTDs, UAS Tdtomato (UAS Tdt) and CAG-nlacZ. Removal of GFP resulted in loss of Tdtomato expression in electroporated patches, as indicated by nlacZ.
Figure 4:
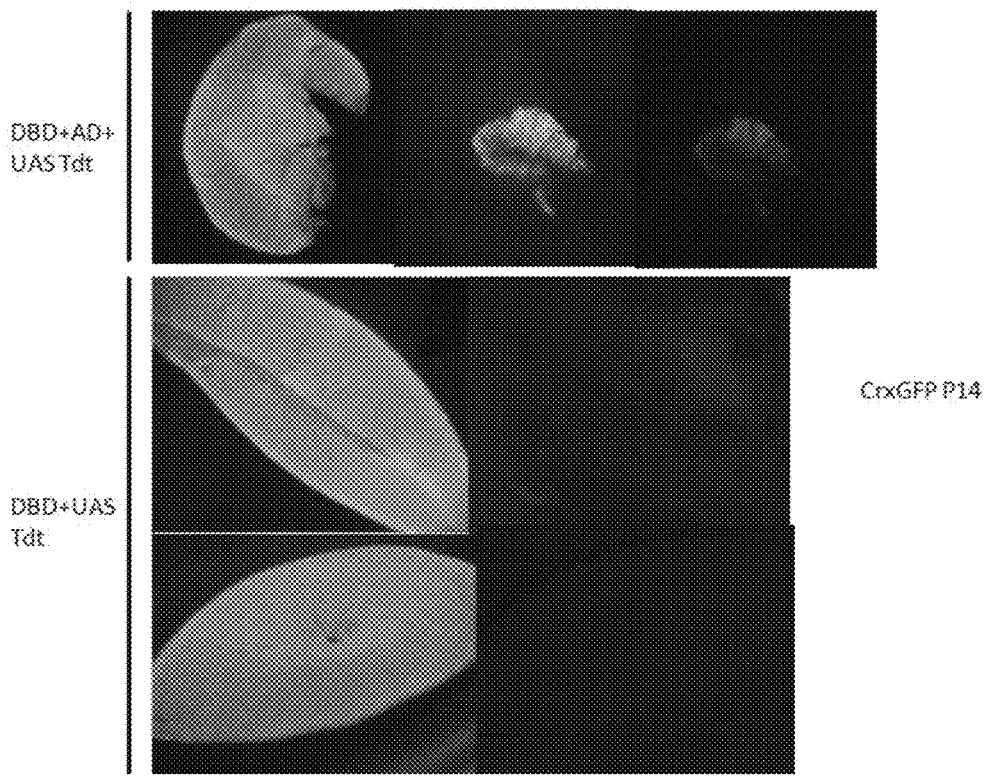
FIG. 4. Retrofitting of transgenic GFP animals with GDTDs. P0 retinas from CrxGFP transgenic mouse were electroporated with GDTDs along with a UAS Tdtomato (UAS Tdt) reporter. At P14, UAS Tdt was detected in the retinas, but not when the activation domain component (AD) of GDTD was removed from the electroporation mix.

The properties of GDTDs can be readily changed and tuned by modifying either the AD or DBD components. The repertoire of GDTDs was expanded with other sequence specificities and properties. GDTDs based on the lexA DBD (Butala et al., 2009) and the rtTA DBD (Zhou et al., 2006) activated reporters bearing their respective binding sequences only when GFP is present (FIG. 2A, FIG. 2B). The transcription activity of rtTA-based GDTDs was further dependent on the level of doxycycline (FIG. 2C). Thus, rtTA-based GDTDs can be controlled spatially by GFP expression patterns, and temporally by doxycycline application. rtTA-GDTDs may overcome the caveat associated with GFP stability.

The critical region for VP16 AD function has been mapped to a 12 amino acid peptide (VP16min) (Baron et al., 1997). This domain can give increasing levels of transcription activation when linked in multiple repeats. The transcription potency of GDTD1/6 could be adjusted by varying the number of VP16min repeats (FIG. 2D).

Overexpression of activation domains can adversely affect cell viability and physiology via 'squelching' of general transcription factors (Gill et al., 1988). It was found that full length VP16 AD had toxic effects on retinal development and so strategies were explored to reduce this problem. First, strong reporter induction was retained by compensating the reduction of VP16min repeats by increasing the number of GBPs fused to the DBD (FIG. 2D). This is expected to reduce cell toxicity by reducing the amount of interaction between the freely available AD and general transcription machinery. Second, the p65 activation domain from NF-kappa-b has been used as a less toxic alternative to VP16 (Rivera, 1998). Indeed, the p65 activation domain was found to serve as a potent AD in this system (FIG. 2E).

Next, it was determined whether a GFP reporter is capable of turning on GDTDs in vivo. Plasmids encoding CAG-GFP, GDTD1/6, UAS Tdtomato, and CAG nLacZ were electroporated into the postnatal day 0 murine retina. At P14, we observed Tdtomato fluorescence in retinas electroporated with GFP and GDTD1/6. In contrast, no signal was detected in those retinas electroporated with an incomplete collection of GFP:GDTD plasmids. GDTD1/6 activity is restricted to GFP-expressing retinal cell types. When the above experiment was repeated with GFP under the control of a rod-specific (Rho) (Matsuda et al., 2004), or a bipolar cell-specific (mGluR6) promoter (Samson et al., 2009), Tdtomato was found to be expressed only in GFP-expressing cells. Electroporated cells labelled by nLacZ, but not GFP, did not express Tdtomato.

In order to use GDTDs for functional studies, it is crucial that the introduced components have minimal effects on cell development, physiology and viability. The overexpression of full length VP16 AD in the retina was observed to cause mispositioning of rod photoreceptors in the retina; rod cell bodies accumulated at the upper half of the outer nuclear layer (ONL) rather than being uniformly distributed along the ONL as they are in controls (data not shown). To overcome this caveat, other ADs which do not contribute to this phenotype were screened. VP16minx2 and p65 AD partially and completely rescued the rod mispositioning phenotype, respectively (data not shown). All subsequent in vivo experiments were performed with GDTDs using p65 AD.

Next it was tested whether GDTDs can be used to derive biologically relevant results. The Otx2 homeobox gene is necessary for photoreceptor specification in the retina. Loss of Otx2 during development leads to a loss of photoreceptors and a gain of cells in the inner nuclear layer (INL). GFP was shown to induce the expression of a UAS-Cre driver, which in turn excised the Otx2 allele in a Otx2 floxed mice. This recapitulated the Otx2 null phenotype by using GDTDs to turn on an UAS-Cre driver in Otx2 floxed retinas ex vivo.

GFP can potentially serve as a universal regulator of synthetic devices in GFP-expressing organisms. It was tested whether existing transgenic GFP mouse lines can be retrofitted for gene manipulation. Crx GFP expresses in rod photoreceptors and bipolar neurons in the retina (Samson et al., 2009; Sato et al., 2007). When P0 Crx GFP retinas were electroporated in vivo with GDTD 1/6, UAS-Tdtomato and nLacZ at P0 and harvested at P14, restriction of Tdtomato expression in GFP positive photoreceptors and bipolar cells was observed. Only GFP-expressing cells had Tdt expression, while all Tdt-positive cells were positive for GFP expression. GFP or Tdt expression was not observed in electroporated amacrine and muller cells. Together, this demonstrates the utility of GFP to control gene expression in GFP-expressing organisms.

Thus, it was demonstrated that GFP can be used not only as a fluorescent reporter, but also as a universal switch to control the activities of synthetic devices. In the mouse, transgenic GFP lines have been made to report the expression of thousands of genes (Gong et al., 2003; Heintz et al., 2004), but gene manipulation studies require the generation of additional transgenic lines expressing transcription factors or site-specific recombinases under the control of the gene's cis-regulatory regions. However, this approach is lengthy, expensive and may not accurately reproduce the original GFP expression pattern. It is now possible to exploit the GFP expressed in these transgenic GFP lines for gene manipulation studies. It is much more economical to create transgenic mouse lines ubiquitously expressing GFP-dependent synthetic devices than to make a transgenic line expressing the gene manipulation tool under every gene's regulatory control. Interesting cell types can be manipulated by simply crossing the cell-specific GFP line to generalized transgenic lines carrying the GFP detector and responder cassettes. The GBPs and/or responder cassettes can also be introduced using viruses or electroporation. This approach may even be applicable to the study of long-living model systems, such as primates, where it is unrealistic to perform sequential genetic crosses for routine experiments. GFP can also now be used as a component for circuit design. Because GFP is freely diffusible in the extracellular matrix, one intriguing possibility is the use of GFP as a ligand for synthetic signaling systems.

Example 2

If a monomer ligand cannot efficiently bring together two fragments that require a specific spatial orientation, ligand multimers may be employed. A GFP dimer was made by splicing by overlap extension PCR. A 12 amino acid linker (GHGTGSTGSGSS; SEQ ID NO:1) was added between two EGFP coding sequences. No changes were made to the EGFP coding sequence. The final PCR product was cloned in place of GFP in the pCAG GFP vector via AgeI/NotI.

Figure 7:
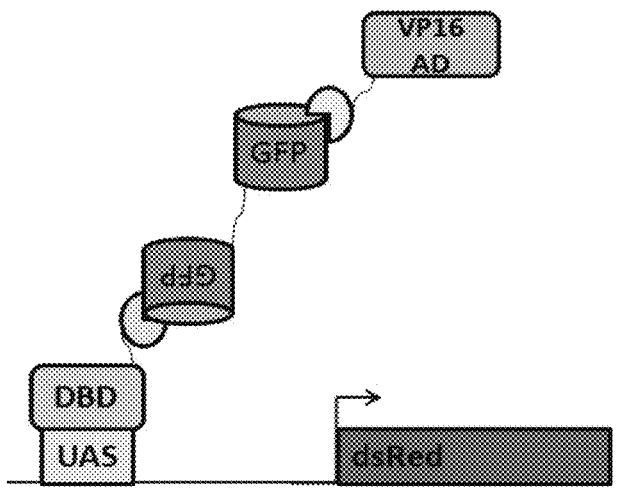
FIG. 7. Schematic of GFP dimer system.
Figure 8:
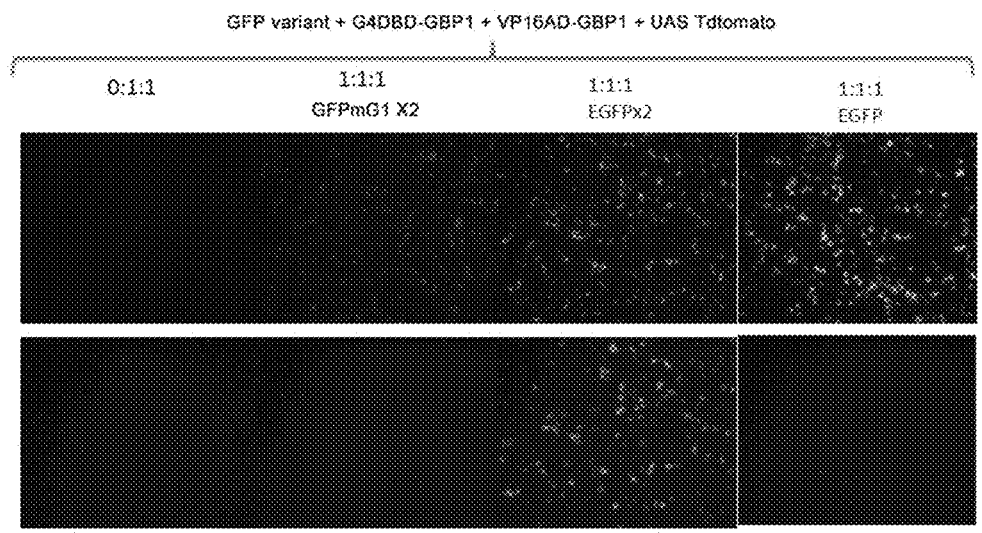
FIG. 8. Activation of UAS-Tdtomato in the presence of dimeric GFP. Transfection of 293T cells with G4DBD-GBP1, VP16AD-GBP1, UAS-Tdtomato, and either EGFPx2, EGFPmG1x2, and EGFP. Molar ratios of GFP variant: DBD: AD are depicted above each condition. 24 hours later, Tdtomato is strongly activated in the presence of EGFPx2, but not in the presence of EGFPmG1x2 or EGFP.

Tdtomato was strongly activated in the presence of EGFPx2, but not in the presence of EGFPmG1x2 or EGFP (FIG. 7). FIG. 8 illustrates dimeric GFP-dependent expression of UAS Tdtomato.

Example 3

Figure 9:
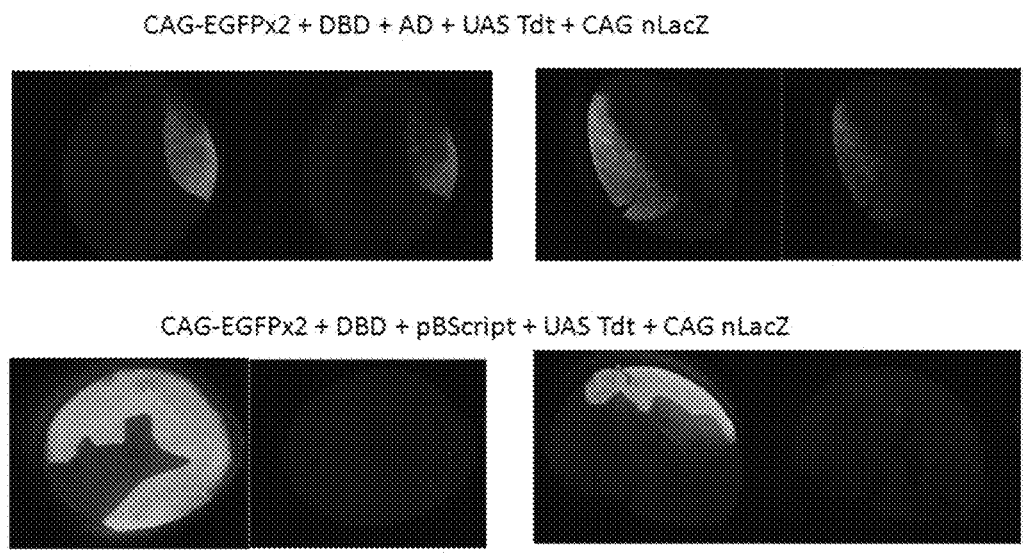
FIG. 9. Activation of UAS Tdtomato by dimeric GFP transcription system in vivo. P0 murine retinas were electroporated with CAG-EGFPx2, G4DBD-GBP1 (DBD), VP16AD-GBP1 (AD), UAS Tdtomato, and CAG nlacZ. pBScript was added in place of AD in the negative control. 14 days later, whole retinas were harvested, showing dimeric GFP-dependent expression of UAS Tdtomato.

Many responder cassettes in transgenic mice are activated by the Cre recombinase. GBP-split Cre constructs (FIG. 9) were made as follows. Two split Cre pairs, 19T to 104L+106D to 343R, and 19T to 59N+60N to 343R, were fused to GBP1, 2, 4, 5, 6 and 7. A 12- or 15-amino acid linker was inserted between GBP and the split Cre fragment. Each split Cre fragment was amplified from pDIRE (Addgene plasmid 26745) (encoding a codon-optimized Cre, or iCre), adding AgeI-koz-NLS-NheI-MfeI on the 5' end and NotI on the 3' end. All fragments were cloned in place of GFP in the pCAG-GFP vector via AgeI/NotI. GBPs were subsequently cloned into these vectors via NheI/MfeI.

Figure 10:
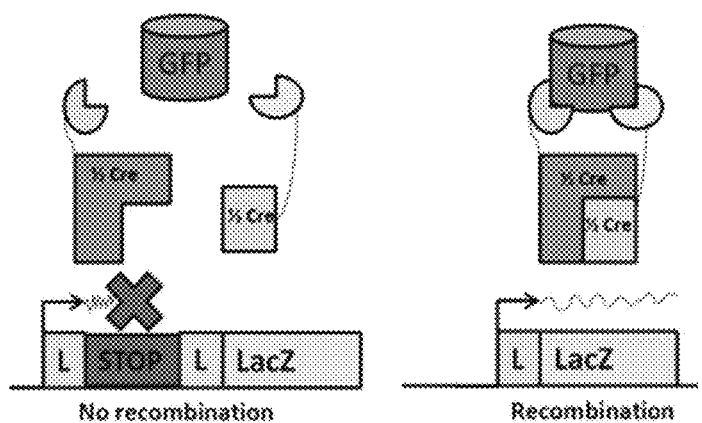
FIG. 10. Concept of a GFP-dependent Cre recombinase. GFP binding proteins (GBP) recognizing non-overlapping epitopes on GFP are fused to split Cre fragments (1/2 Cre). GFP recruits the two GBP:split Cre fragments to reconstitute recombinase activity. To assay recombination, a reporter gene (LacZ) is placed behind a loxP-STOP-loxP cassette. STOP is a transcriptional terminator which prevents the transcription of the downstream reporter gene. Reconstituted Cre recombinase will recognize loxP (L) and induce removal of the L-STOP-L cassette, leading to transcription and activation of the reporter.
Figure 11:
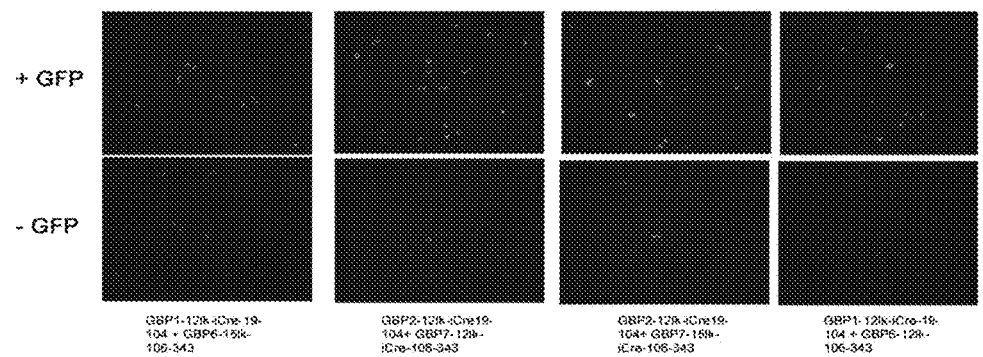
FIG. 11. GFP-dependent split Cre. 293T cells were transfected with the indicated split Cre pairs, pCALNLDsRed, and with or without GFP. Cells were imaged 26 hours later for activation of the pCALNLDsRed reporter.
Figure 12:
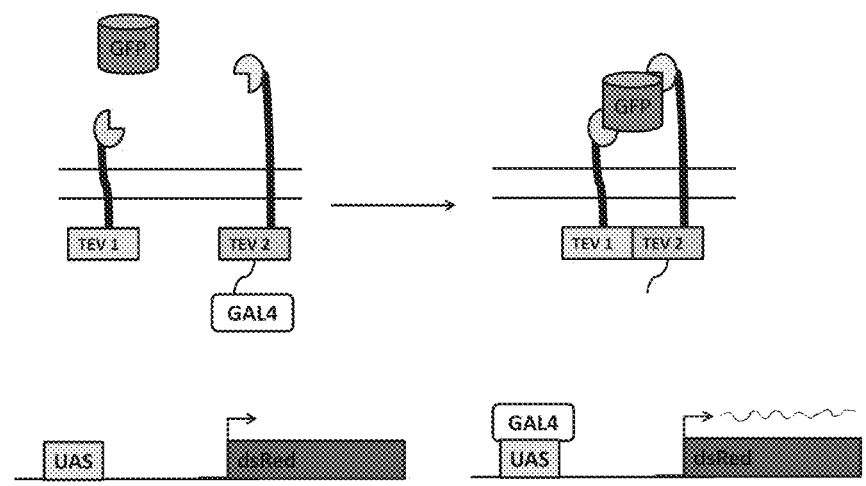
FIG. 12. Schematic of another system of the invention. GFP links two transmembrane GBP fusion components, resulting in reconstitution of protease (e.g., TEV) activity, which in turn cleaves a recognition sequence and releases GAL4, which can then activate genes in the nucleus.

GBP Split Cre constructs were combined in many possible pairs and transfected into 293T cells along with pCALNLdsRed (Addgene plasmid 13769) (FIG. 10). pCAG-GFP or pBluescript were included for duplicate transfections for each split Cre pair.

Example 4

As described above, GBP pairwise combinations, e.g., GBP1+GBP6 and GBP2+GBP7, can be used to construct a GFP-dependent transcription factor in cells. These data implied that each GBP pair could individually co-occupy GFP and allow the recruitment of tethered proteins. These GBP pairs may also be able to induce the formation of split-proteins such as recombinases and proteases. As proof of concept, a GFP-dependent Cre was selected given its potential use for taking advantage of all loxP-based expression cassettes built for the mouse and other model organisms. First, fusion constructs bearing GBP and split Cre components were screened. Although GFP-dependent Cre-recombination was observed with reporters, the recombination efficiency was less than desirable and high background was often observed (data not shown). One explanation for the low efficiency lies in the requirement for formation of a three-component GFP-split-Cre complex in a specific orientation. To avoid this issue, and to increase efficiency, GFP was used to induce the splicing of functional, single molecule Cre recombinases via the intein protein splicing modules. Fusion constructs bearing GBP with the artificially split S. cerevisiae vacuolar ATPase (VMA) intein and split Cre components were constructed (see FIG. 13) (Cre-recombinase Dependent on GFP(CRE-DOG)). Of the tested combinations, the GBP2+GBP7 combination gave 20 to 60 fold induction of recombination in a GFP-dependent manner, along with reasonably low background in the absence of GFP, at 3-4 fold above control, suggesting that the GBP2-GFP-GBP7 complex orientates the inteins in an orientation suitable for efficient protein splicing.

Recombination only occurred in the presence of all components, but not when any component was removed from the transfection. GBP2+GBP7 based T-DDOGs can facilitate transcription in response to the GFP derivatives cyano (CFP) and yellow (YFP) fluorescent proteins, and was also able to induce recombination in the presence of CFP and YFP. In addition, CRE-DOG did not respond to the presence of dsRed or its derivatives, mCherry and tdTomato. (FIG. 15)

GFP-dependent recombination could be due to the mere formation of a GFP-dependent complex, but not the splicing of Cre. To determine whether protein splicing is required, the ability of a mutant CRE-DOG to facilitate recombination was evaluated. Mutations known to abolish intein splicing activity were introduced into constructs. GFP-dependent recombination was not or only slightly affected with mutant CRE-DOG, suggesting against a requirement for protein splicing. To more directly determine whether Cre can be spliced, full-length Cre formation was probed in the presence or absence of GFP. There was a failure to observe the appearance of an expected 34 kDa band in the presence of GFP, suggesting against protein splicing as being involved in mediating GFP-dependent recombination. Lastly, removal of intein elements from CRE-DOG had an adverse effect on the GFP-dependency of CRE-DOG, suggesting that inteins are contributing to the desired property of the system (FIG. 16)

To assess whether CRE-DOG is useful for in vivo studies, its ability to induce GFP-dependent recombination was examined in the mouse retina. CAG-GFP along with CRE-DOGs and a floxed-dsRed reporter were electroporated into P0 mouse retinas and GFP-dependent activation of dsRed at P14 was found. Further, CRE-DOG can act in a cell-specific manner, as the activation of dsRed was restricted to rod photoreceptors when Rho-GFP is used in place of CAG-GFP. In contrast to the T-DDOG system, which carries the caveat of being potentially toxic to cells as a consequence of squelching phenomenon caused by activation domains, CRE-DOG did not induce any noticeable defects in retinal cell phenotypes. (FIG. 17).

Figure 18:
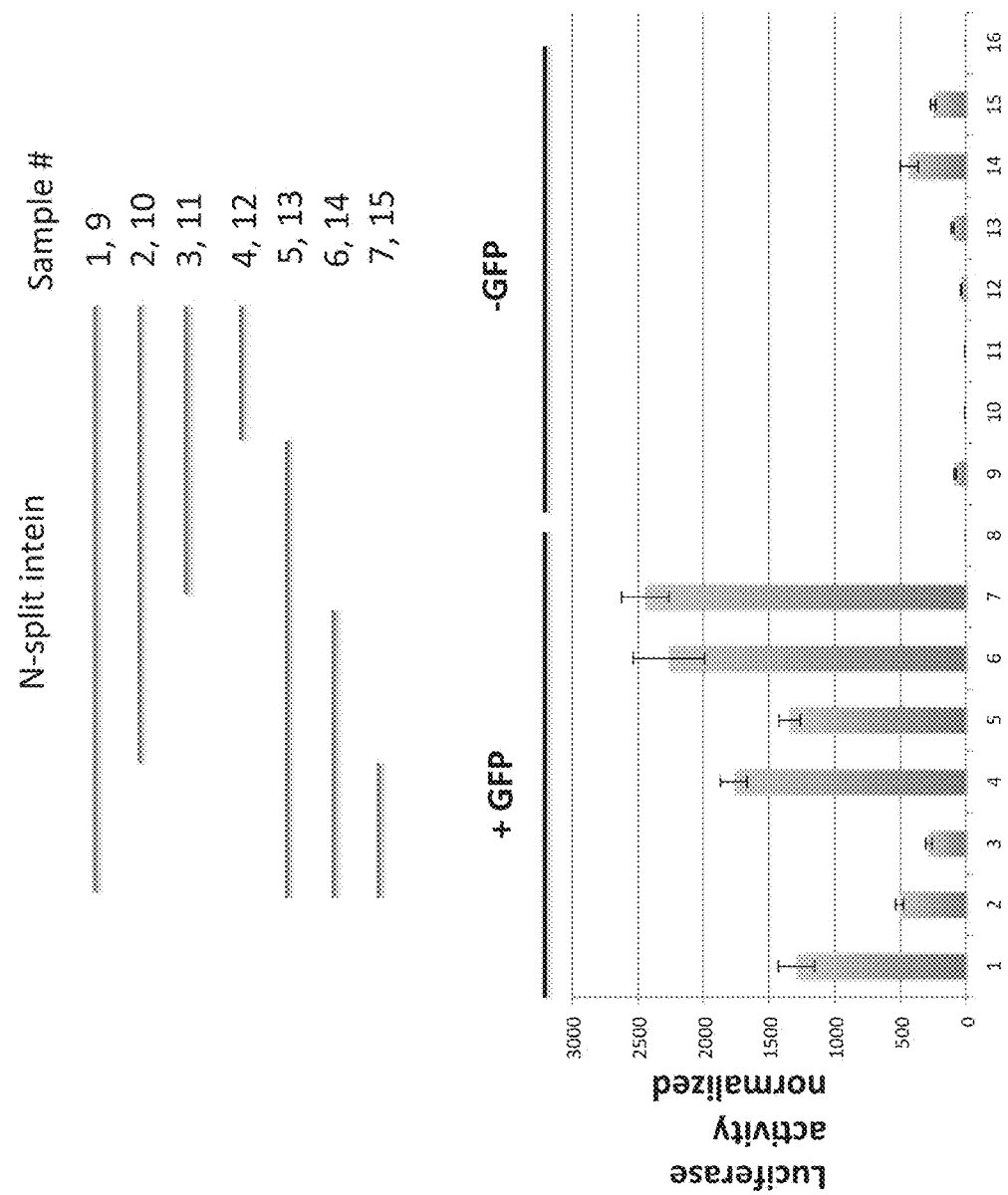
FIG. 18. Schematic of N-terminal inteins (including truncated versions) employed in GFP-dependent activation of a floxed luciferase reporter.

FIG. 18 shows results of an assay to determine the core intein N-terminal sequence for enhanced activity (Cre recombinase) relative to a 184 amino acid N-terminal intein fragment. Deletions were made from the N-terminal and C-terminal end of the N-terminal intein fragment. All fragments, even the smallest one (46 amino acids in length), resulted in activity. The smallest fragments were composed of either beta strands or alpha helices.

Thus, it was demonstrated that a GFP-dependent Cre recombinase could be obtained by coupling to an intein splicing system. Although inteins play a role in mediating the GFP-dependency of the system, protein splicing was not required. Such a system now enables the use of GFP to induce recombination of loxP-based cassettes that can be transiently delivered as DNA plasmids, viruses, or in a transgenic animal carrying loxP-based alleles. The immediate beneficiaries are those studying model organisms, with transgenic GFP lines made—these scientists will be able to retrofit their existing transgenic GFP lines for cell-specific gene manipulation. This system may further be applied as components in a variety of plausible synthetic circuits. Therefore, artificially-derived protein binders are useful for protein-inducible enzymes.

REFERENCES

Baron et al., *Nucleic Acids Res.*, 25:2723 (1997).
Berg et al., *Nat. Methods*, 6:161 (2009).
Boch et al., *Nat. Biotech.*, 29:143 (2011).
Butala et al., *Cell. Mol. Life. Sci.*, 66:82 (2009).
Chalfie et al., *Science*, 263:802 (1994).
Emerson and Cepko, *Dev. Biol.*, 360:241 (2010).
Gill et al., *Nature*, 334:721 (1988).
Gong et al., *Nature*, 425:917 (2003).
Heintz, *Nat. Neurosci.*, 7:483 (2004).
Ho et al. *Nature*, 382:822 (1996).
Kim et al., *J. Neurosci.*, 28:7748 (2008).
Kirchhofer et al., *Nat. Struct. Mol. Biol.*, 17:133 (2010).
Matsuda and Cepko, *Proc. Natl. Acad. Sci. USA*, 101:16 (2004).
Miyawaki et al., *Nature*, 388:882 (1997).
Ogawa et al., *Proc. Natl. Acad. Sci. USA*, 92:11899 (1995).
Olson and Roberts, *Prot. Sci.*, 16:476 (2007).
Patterson and Lippincott-Schwartz, *Science*, 297:1873 (2002).
Pollock et al., *Curr. Opin. Biotechnol.*, 13:459 (2002).
Rivera, *Methods*, 14:421 (1998).
Rothbauer et al., *Mol. Cell. Proteomics*, 7:282 (2008).
Rothbauer et al., *Nat. Methods*, 3:887 (2006).
Sadowski et al., *Nature*, 335:563 (1988).
Samson et al., *Dev. Dyn.*, 238:3218 (2009).
Sato et al., *Genesis*, 45:502 (2007).
Shaner et al., *Nat. Methods*, 2:905 (2005).
Trinkle-Mulcahy et al., *J. Cell Biol.*, 183:223 (2008).
Tsien, *Annu Rev. Biochem.*, 67:509 (1998).
Zhou et al., *Gene Ther.*, 13:1382 (2006).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method comprising:

providing a non-human transgenic mammal i) expressing in at least some cells of the mammal a fluorescent protein from a first expression cassette that is stably integrated into the genome of the mammal, wherein the first expression cassette comprises an open reading frame for the fluorescent protein, and ii) having a nucleic acid segment of interest that is capable of binding a preselected protein and that is linked to an open reading frame for a gene product;

introducing into the at least some cells of the mammal, one or more expression cassettes encoding two different fusion proteins, so as to result in the expression of the two different fusion proteins in the at least some cells of the mammal, wherein the first fusion protein comprises a portion of a first selected protein linked to a first protein linker linked to a first binding protein for the fluorescent protein, wherein the second fusion protein comprises a second portion of a second selected protein linked to a second linker linked to a second binding protein for the fluorescent protein, wherein the portion of the first selected protein and the portion of the second selected protein together reconstitute the preselected protein that binds to the nucleic acid segment of interest, wherein the first and second binding proteins comprise portions of an antibody that binds the fluorescent protein, wherein the portion of the first selected protein is a DNA binding domain, a transcriptional activator, a transcriptional repressor, or comprises a portion of an enzyme that binds nucleic acid or catalyzes a reaction, wherein the portion of the second selected protein is a DNA binding domain, a transcriptional activator, a transcriptional repressor, or comprises a portion of an enzyme that binds nucleic acid or catalyzes a reaction, and wherein the first and second binding proteins bind to the fluorescent protein and reconstitute the preselected protein; and detecting the presence, amount, or location of the fluorescent protein in the at least some cells of the mammal or detecting an alteration in the expression of the gene product in the mammal as a result of the binding of the preselected protein to the nucleic acid sequence of interest when the preselected protein comprises the transcriptional activator, the transcriptional repressor, or the portion of the enzyme that catalyzes a reaction relative to cells of a mammal that do not have or express the fusion proteins or do not express green fluorescent protein.

2. The method of claim 1 wherein the mammal comprises a second expression cassette.

3. The method of claim 2 wherein the second expression cassette is introduced into the mammal concurrently with the one or more expression cassettes encoding the two different fusion proteins.

4. The method of claim 2 wherein the genome of the mammal comprises the second expression cassette.

5. The method of claim 1 wherein the preselected protein comprises a recombinase and wherein the mammal comprises a second expression cassette comprising the nucleic acid segment which comprises recognition sites for the recombinase.

6. The method of claim 1 wherein the first expression cassette comprises a tissue-, cell- or lineage-specific promoter.

7. The method of claim 1, wherein the preselected protein, when reconstituted, is an enzyme and when in the presence of the fluorescent protein catalyzes a reaction.

8. The method of claim 1, wherein the first portion in the first fusion protein is a DNA binding domain and the first portion in the second fusion protein is a transcriptional activator, transcriptional repressor, or nuclease.

9. The method of claim 1 wherein the mammal is a mouse.

10. The method of claim 1 wherein the gene product is a beta-galactoside, beta-lactamase, luciferase or red fluorescent protein.

11. The method of claim 1, wherein the enzyme is a nuclease.

12. The method of claim 1 wherein the first and second protein linkers are portions of an intein.

13. The method of claim 1, wherein the enzyme is a recombinase.

14. The method of claim 1, wherein the fluorescent protein is a green fluorescent protein, a yellow fluorescent protein, or a red fluorescent protein.

* * * * *

SEQUENCE LISTING

```
<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: A synthetic polypeptide linker

<400> SEQUENCE: 1

Gly His Gly Thr Gly Ser Thr Gly Ser Gly Ser Ser
1               5                   10

<210> SEQ ID NO 2
<211> LENGTH: 35
<212> TYPE: PRT
<213> ORGANISM: Artificial Sequence
<220> FEATURE:
<223> OTHER INFORMATION: A synthetic DNA binding polypeptide

<400> SEQUENCE: 2

Leu Thr Pro Glu Gln Val Val Ala Ile Ala Ser Asn Ile Gly Gly Lys
1               5                   10                  15
```

```
Gln Ala Leu Glu Val Thr Val Gln Arg Leu Leu Pro Val Leu Leu Gln
            20                  25                  30
Ala His Gly
        35
```